(12) United States Patent
Zirps et al.

(10) Patent No.: US 7,189,247 B1
(45) Date of Patent: Mar. 13, 2007

(54) ENDOSCOPIC BAND LIGATOR

(75) Inventors: Christopher T. Zirps, Sharon, MA (US); Timothy R. Membrino, Acton, MA (US); Scott Reed, Monroe, CT (US); Ernest Corrao, Jr., Bethel, CT (US); Stephen Maguire, Huntington, CT (US); Eric Mears, South Bristol, ME (US); David J. Copeland, Milton, MA (US); John S. Murphy, North Reading, MA (US); Joseph Logan, Trumbull, CT (US); Sean J. Silva, North Reading, MA (US); Stephen J. Yardan, Branford, CT (US)

(73) Assignee: Conmed Endoscopic Technologies, Inc., Billerica, MA (US)

( * ) Notice: Subject to any disclaimer, the term of this patent is extended or adjusted under 35 U.S.C. 154(b) by 128 days.

(21) Appl. No.: 10/656,083

(22) Filed: Sep. 5, 2003

Related U.S. Application Data

(60) Provisional application No. 60/408,555, filed on Sep. 6, 2002.

(51) Int. Cl.
*A61B 17/04* (2006.01)
(52) U.S. Cl. ..................... 606/140; 606/141
(58) Field of Classification Search ......... 606/140–141
See application file for complete search history.

(56) References Cited

U.S. PATENT DOCUMENTS

| | | | | |
|---|---|---|---|---|
| 4,226,239 A | * | 10/1980 | Polk et al. | 606/141 |
| 4,230,116 A | * | 10/1980 | Watson | 606/141 |
| 4,735,194 A | * | 4/1988 | Stiegmann | 600/104 |
| 4,788,966 A | * | 12/1988 | Yoon | 128/831 |
| 5,201,908 A | | 4/1993 | Jones | |
| 5,259,366 A | | 11/1993 | Reydel et al. | |
| 5,275,151 A | | 1/1994 | Shockey et al. | |
| D344,334 S | | 2/1994 | Dulebohn et al. | |
| 5,325,746 A | | 7/1994 | Anderson | |
| 5,356,416 A | * | 10/1994 | Chu et al. | 606/140 |
| 5,382,254 A | | 1/1995 | McGarry et al. | |
| 5,383,875 A | | 1/1995 | Bays et al. | |
| 5,409,478 A | | 4/1995 | Gerry et al. | |

(Continued)

OTHER PUBLICATIONS

U.S. Appl. No. 10/656,085, filed Sep. 5, 2003, Zirps et al.

(Continued)

*Primary Examiner*—Gary Jackson
(74) *Attorney, Agent, or Firm*—Proskauer Rose LLP

(57) ABSTRACT

The present invention provides a ligating band dispenser that is mounted on the distal end of an endoscope. The ligator is configured to deliver multiple ligating bands to a plurality of internal sites in a patient. The ligating bands are carried on a tubular band carrier member that is retractable relative to the distal end of the endoscope in order to preserve visibility through the endoscope during navigation, then extendable to define a suction chamber for tissue aspiration during band delivery. A tubular band driver member is slidable over the band carrier member and engages bands individually to push them off the distal end of the band carrier and onto a selected treatment site. A single-hand operated control handle for selectively operating the extension of the band carrier and movement of the band driver to release a band is also provided and is slidably and removably mounted to the endoscope shaft.

14 Claims, 27 Drawing Sheets

U.S. PATENT DOCUMENTS

| | | | |
|---|---|---|---|
| 5,447,148 A | 9/1995 | Oneda | |
| 5,470,328 A | 11/1995 | Furnish et al. | |
| 5,498,256 A | 3/1996 | Furnish | |
| 5,503,616 A | 4/1996 | Jones | |
| 5,507,797 A | 4/1996 | Suzuki et al. | |
| 5,569,268 A * | 10/1996 | Hosoda | 606/140 |
| 5,601,568 A | 2/1997 | Chevillon et al. | |
| D378,611 S | 3/1997 | Croley | |
| 5,624,431 A | 4/1997 | Gerry et al. | |
| 5,643,175 A | 7/1997 | Adair | |
| D383,539 S | 9/1997 | Croley | |
| 5,662,588 A | 9/1997 | Iida | |
| D385,350 S | 10/1997 | Furnish | |
| 5,690,645 A | 11/1997 | Van Erp | |
| 5,725,536 A | 3/1998 | Oberlin et al. | |
| 5,735,793 A | 4/1998 | Takahashi et al. | |
| 5,788,715 A * | 8/1998 | Watson et al. | 606/140 |
| 5,888,191 A | 3/1999 | Akiba | |
| 5,980,537 A * | 11/1999 | Ouchi | 606/140 |
| 5,993,384 A | 11/1999 | Lunsford et al. | |
| 6,059,719 A | 5/2000 | Yamamoto et al. | |
| 6,149,659 A * | 11/2000 | Ahmed | 606/140 |
| 6,306,081 B1 | 10/2001 | Ishikawa et al. | |
| 6,340,344 B1 | 1/2002 | Christopher | |
| D459,474 S | 6/2002 | Bratt et al. | |
| 6,436,108 B1 * | 8/2002 | Mears | 606/140 |
| 6,464,685 B1 * | 10/2002 | Suzuki et al. | 604/534 |
| 6,576,005 B1 | 6/2003 | Geitz | |
| D480,807 S | 10/2003 | Yardan et al. | |
| 6,685,713 B1 * | 2/2004 | Ahmed | 606/140 |
| 6,730,101 B1 * | 5/2004 | Peifer et al. | 606/140 |
| 2001/0027312 A1 | 10/2001 | Bacher et al. | |
| 2003/0167062 A1 | 9/2003 | Gambale et al. | |
| 2003/0171651 A1 | 9/2003 | Page et al. | |
| 2003/0171760 A1 | 9/2003 | Gambale | |
| 2003/0208209 A1 | 11/2003 | Gambale et al. | |
| 2004/0034371 A1 | 2/2004 | Lehman et al. | |

OTHER PUBLICATIONS

U.S. Appl. No. 10/656,557, filed Sep. 5, 2003, Zirps et al.
U.S. Appl. No. 10/658,135, filed Sep. 8, 2003, Aznoian et al.
U.S. Appl. No. 10/658,619, filed Sep. 8, 2003, Gambale et al.

* cited by examiner

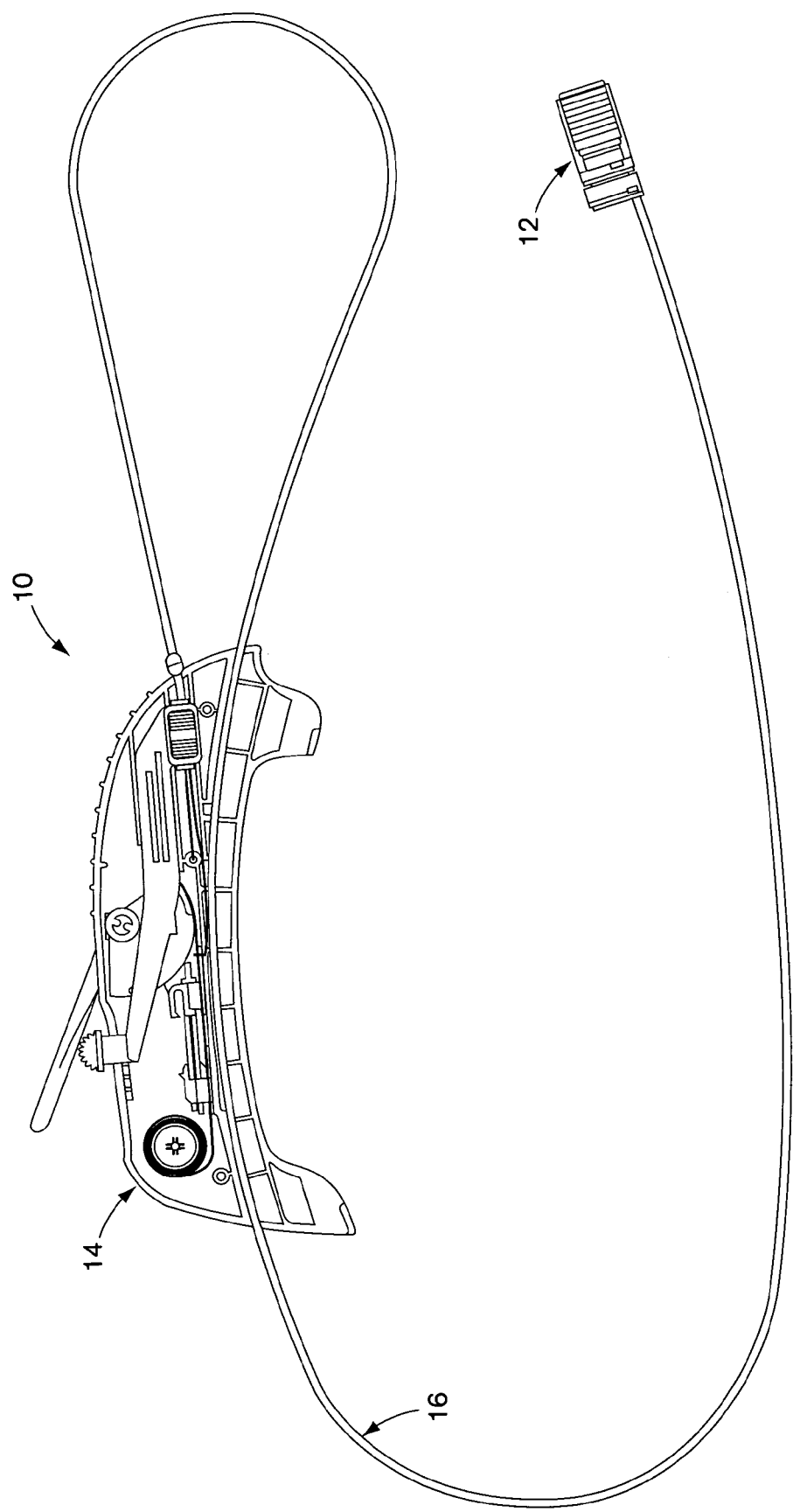

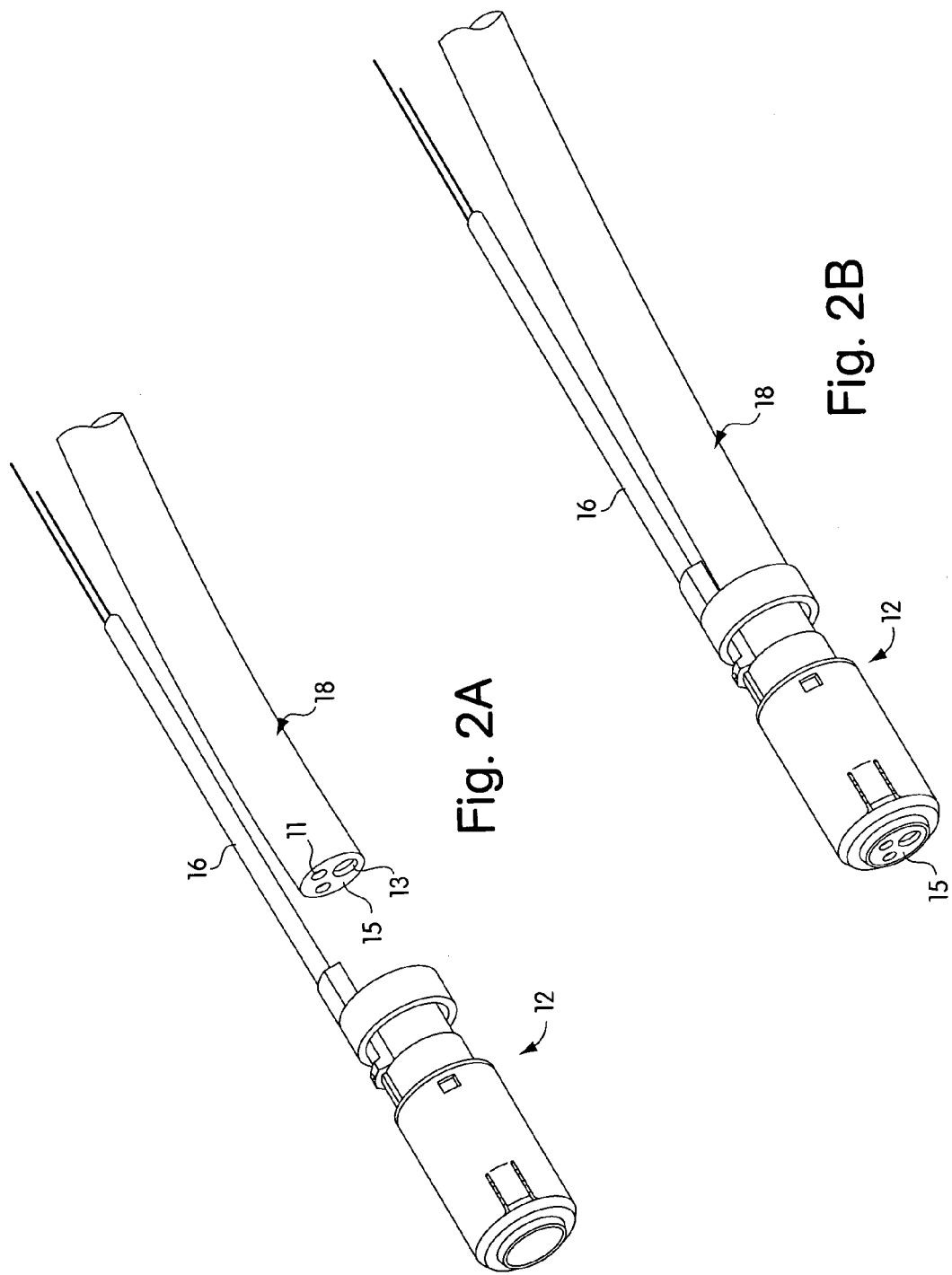

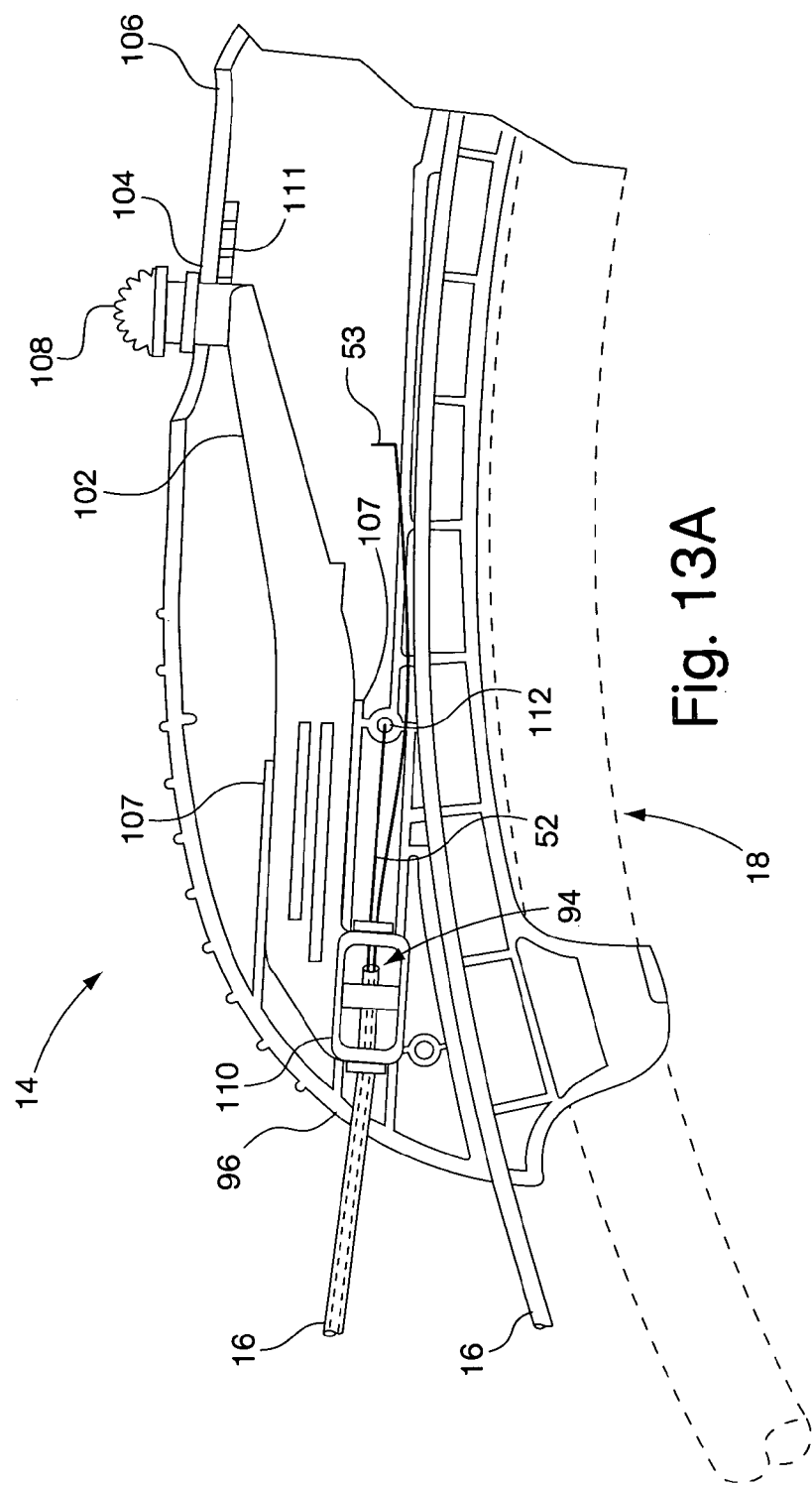

ENDOSCOPIC BAND LIGATOR

This application claims the benefit of provisional application 60/408,555 filed Sep. 6, 2002.

FIELD OF THE INVENTION

The present invention relates to medical ligating instruments. In particular, the invention relates to multiple band endoscopic band ligating devices.

BACKGROUND OF THE INVENTION

Ligation is a procedure in which a thread, wire or band are applied around a tissue structure or area to constrict it thereby preventing flow of blood or other body fluids. Band ligation involves applying a highly elastic band around a tissue site to constrict it. Ligation may be used to treat varices, polyps, hemorrhoids, or other lesions. After application of a ligator at the treatment site, bleeding is stopped and the tissue below the ligature then begins to heal and fuse together while the tissue above the ligature becomes necrotic and eventually separates from the site. Band ligators are devices that are used to deliver an elastic band in an expanded configuration to a tissue location then release it around the treatment site permitting it to return to its relaxed orientation to constrict the tissue. Band ligators have been adapted to be attached to the distal end of endoscopes to facilitate application of bands to treatment sites in natural body lumens such as the esophagus or rectum. Endoscopic band ligators have become especially useful in treating esophageal varices. A band ligator attached to the distal end of a flexible viewing endoscope can be navigated, visually, directly to a varix location to accurately apply a ligating band.

Multiple band endoscopic ligators are shown in U.S. Pat. Nos. 6,042,591, 6,136,009 and 6,436,108, all of which are incorporated by reference herein. Those multiple band ligators operate to dispense ligating bands by arranging a plurality of bands along an inner cylinder that is mounted over the distal end of an endoscope and reciprocally operating an outer cylinder, slidable over the inner cylinder to push off bands individually from the inner cylinder. Projecting fingers extending radially inward from the outer cylinder engage the bands individually so that they may be pushed off one at a time onto the aspirated varix. In moving the outer cylinder longitudinally relative to the inner cylinder and several bands, a performance concern is being able to reliably position the inwardly projecting fingers behind a single ligating band and reliably discharging that single band to the varix. Because of inherent inaccuracies in the remote operation of the outer cylinder, more than one band could be inadvertently released at a single site or the device could fail to release any bands at the location. Further frustrating this problem is the fact that the physician may not realize that a single band is not successfully released at the desired location. It is an object of the present invention to improve the reliability with which a single band can be released from the ligating device at a treatment site.

Another concern with the accurate operation of a multiple band endoscopic ligating device centers on the physician's ability to remotely control the device from outside the patient. Control handles for operating ligating devices have been somewhat primitive and may require two hands to operate. Two handed operation of the ligator control handle is especially problematic in the endoscopic context because at least one hand must be used to operate endoscope controls for articulating the distal end of the endoscope so that it may be properly navigated. As a result, operation of know endoscopic band ligators typically requires two people to operate all the necessary controls at the proximal end of the endoscope. It is an object of the present invention to provide an endoscopic band ligator control handle that can be operated with a single hand while maintaining control of the endoscope shaft.

Another concern with the remote operation of the band ligating device is the accuracy with which the band dispenser component can be operated to insure release of a single band. Cable operated band dispensers lose tactile feel and accurate movement due to the flexibility inherent in the cable and in the unstable sliding movement of the small ligator components that move to release the bands. More accurate operation of the band ligator controls would enhance the reliability of the band release from the device. It is an object of the invention to improve the remote operation of the band ligator components for accurate band release.

SUMMARY OF THE INVENTION

The inventive device is an endoscopic accessory that attaches to the distal end of a viewing endoscope and is used to apply ligating bands to tissue areas. The device is useful in the treatment of tissue areas accessible through a natural body lumen or cavity such as esophageal varices. Esophageal varices are dilated veins along the surface of the lower end of the esophagus that are prone to bleeding and ulceration. The varices are most easily reached and treated using a flexible viewing endoscope.

The inventive band ligator device comprises three coaxially arranged cylinders that are slidable relative to each other. An innermost cylinder mounts over the distal end of an endoscope and provides a base member for the band ligator components. The middle cylinder and outer cylinder slide relative to the innermost cylinder to allow the band ligator to be retracted proximally from the distal face of an endoscope during navigation to a treatment site, then extended distally relative to the distal face of the endoscope to create a vacuum chamber into which a tissue portion may be aspirated during ligation. The outermost cylinder is then slidable relative to the middle cylinder to dispense a ligating band. Inwardly projecting fingers of the outer cylinder engage each band individually. Circumferential ridges around the middle cylinder serve to hold the bands in position until they are intentionally dislodged by the relative movement of the outer cylinder and projecting fingers. After dispensing a band the outer cylinder automatically recoils back on the middle cylinder and the fingers ride over the next distal band and become positioned just proximal to it, in readiness to push it distally off the middle cylinder at the next treatment site.

The band ligating device is operated by a control handle slidably positioned on the exterior of the endoscope outside of the patient. The control handle is joined to the ligator by control cables that extend externally along the endoscope shaft to leave the working channels of the endoscope free for other uses such as aspiration or scelerothopic injection. The control handle provides operating mechanisms with distinct ranges of travel that enable a user to actuate the extension-retraction function and band delivery function of the ligator with accuracy. The handle is further configured to permit the user to grasp the endoscope as well as the handle in a single hand so that control of the endoscope shaft and operation of the ligator can be achieved with one hand and control of the distal end of the endoscope can be maintained by controls held with the other hand.

It is an object of the present invention to provide an endoscopic band ligator that can be operated to release individual ligating bands accurately based on the commands of the user.

It is another object of the present invention to provide an endoscopic band ligator having a control handle that is easy to manipulate with a single hand in conjunction with maintaining control over the endoscope shaft.

It is another object of the present invention to provide an endoscopic band ligator that is remotely controlled by mechanisms extending proximally from the ligator external to the endoscope leaving the working channels of the endoscope free for complete aspiration or for advancement of other treatment devices.

It is another object of the invention to provide a method of endoscopically applying multiple ligation bands that requires simplified inputs by the user on a control handle that operates the distally mounted ligator.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 1 is a partial sectional illustration of the endoscopic band ligator of the present invention;

FIG. 2A is an isometric illustration of the distal portion of the band ligator prior to mounting on an endoscope;

FIG. 2B is an isometric illustration of the distal portion of the band ligator mounted on the distal end of an endoscope;

FIGS. 13A and 13B are a detailed sectional view of the control handle detailing the thumb slide end of related components.

DESCRIPTION OF THE ILLUSTRATIVE EMBODIMENTS

The band ligator 10, shown in FIG. 1, comprises a working distal portion 12 joined to a control handle 14 via a control sheath 16. The distal portion 12 may be removably mounted to the exterior surface of the distal end of the endoscope. The distal portion 12 is configured to deliver ligating bands to internal tissue locations, such as at varices in order to prevent bleeding at those sites. The distal portion is operated by control wires slidable through sheath 16, which extends proximally, external to the endoscope to the control handle 14. The handle is slidably and removably attached to the exterior of the endoscope shaft. The ligator device is configured to minimize interference with the viewing capability of the endoscope: utilizing transparent components and a retracted mounting configuration on the scope that avoids obstruction of the distal face and viewing lens during navigation to a treatment site.

Figure 1A:
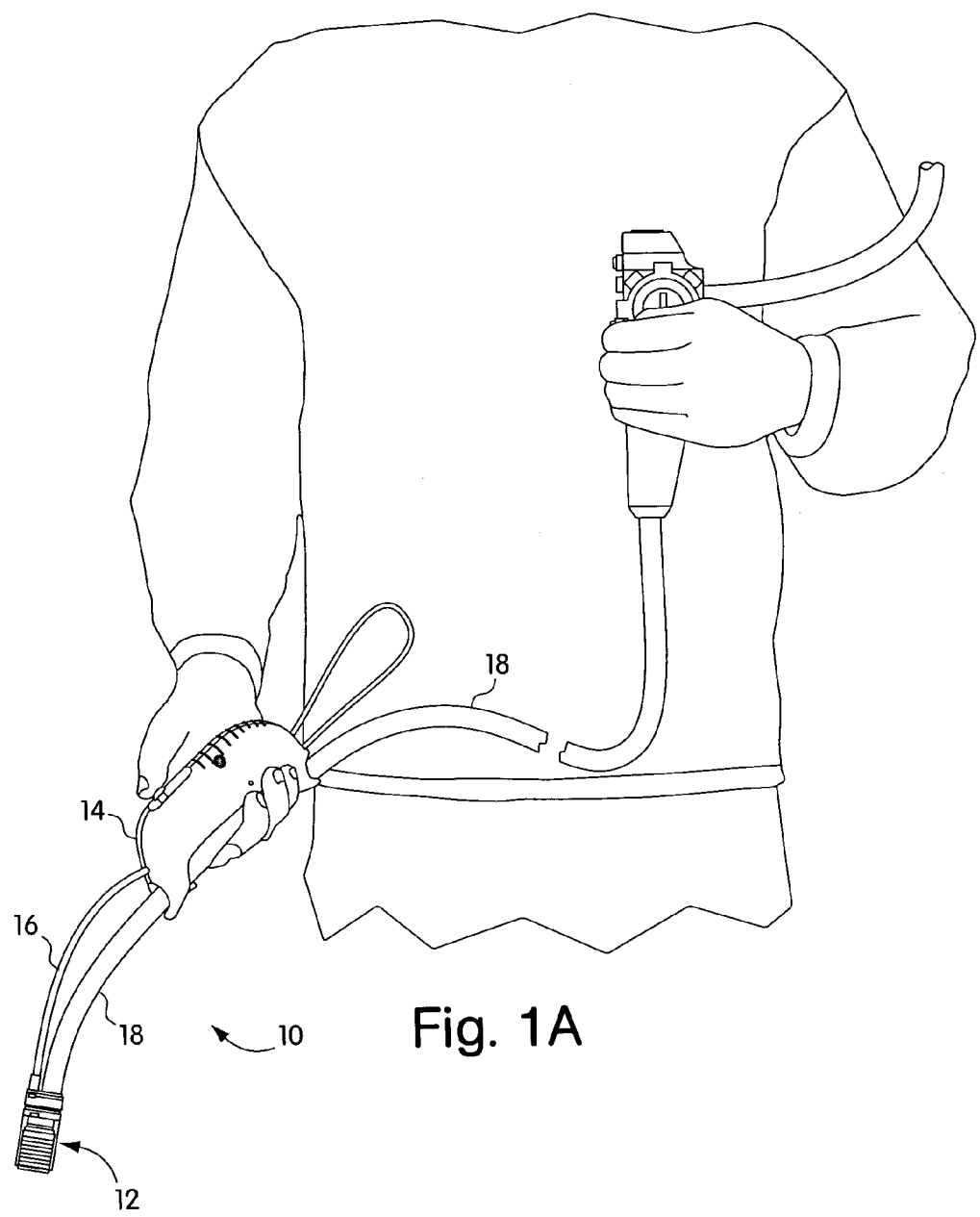
FIG. 1A is an illustration of an operator grasping an endoscope control in the left-hand and the control handle for the band ligator of the present invention in the right hand.
Figure 1B:
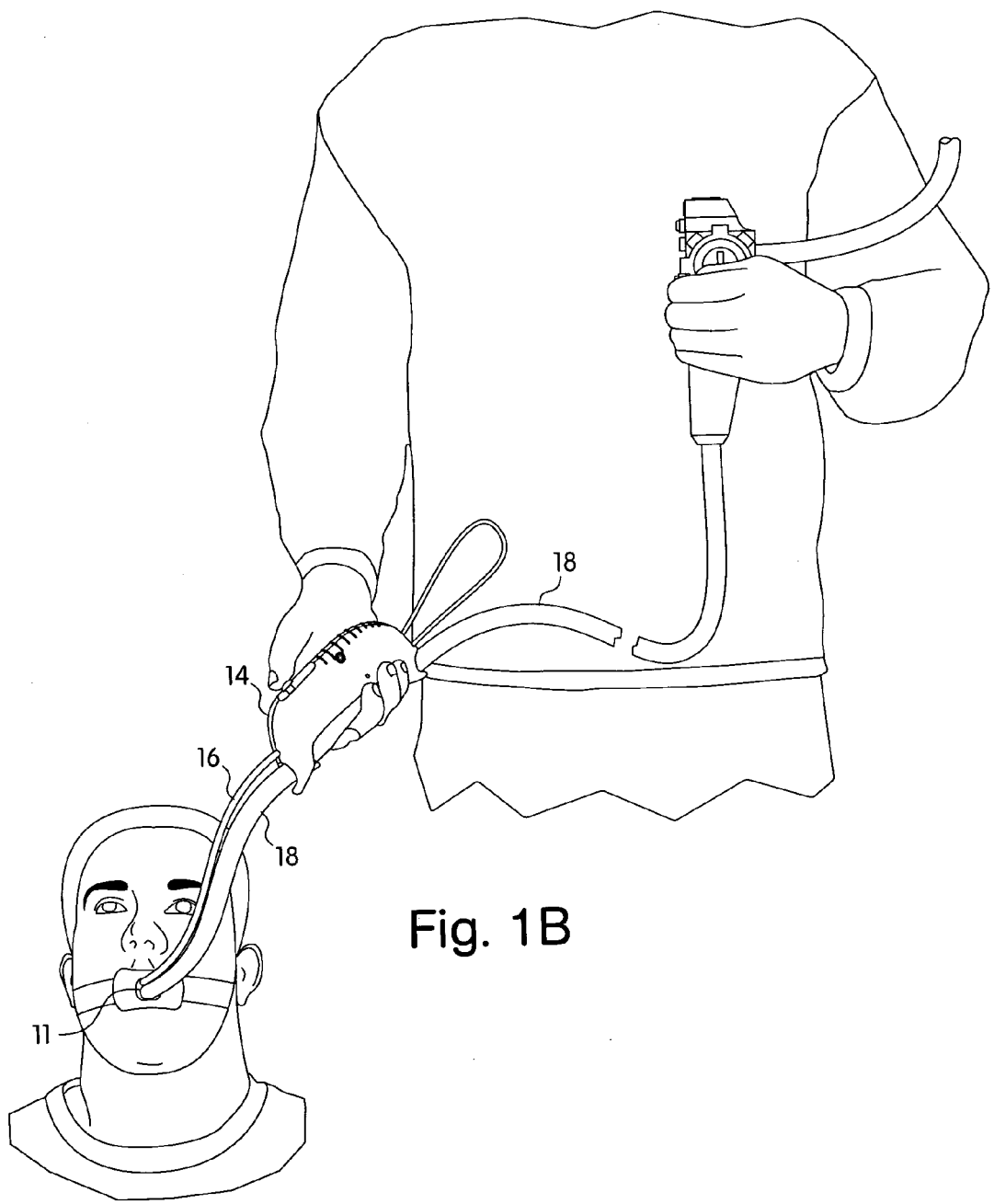
FIG. 1B is an illustration of an operator inserting into a patient the band ligator of the present invention mounted on an endoscope.

In an exemplary use of the device 10 such as treatment of esophageal varices, the distal end of the endoscope 18 with the distal portion of the ligator 12 attached is advanced through a patient's mouth 11 and down the esophagus as shown in FIGS. 1A and 1B. Varices are located visually with the endoscope. When a varix site is located, the distal end of the flexible endoscope is articulated to navigate the distal face of the scope to the varix location. Vacuum is then applied through the endoscope to gather up a section of tissue surrounding the varix into the ligator distal portion 12 and an elastic ligating band is advanced from the ligator device onto and around the gathered tissue to stop bleeding. A detailed description of the structure of the band ligator and its control handle appears below.

The distal portion 12 of the ligator device is slidably mounted onto a distal end of an endoscope 18 as is shown in FIGS. 2A and 2B. The distal portion 12 is backloaded onto the distal end 18 of the scope and slid proximally so that the distal end of the distal portion is substantially flush with the distal face 15 of the scope. The inside surface of the distal portion may be formed with a radially inward projecting lip at its distal end to catch the face of the endoscope and ensure proper mounting. The distal portion 12 of the device is frictionally retained on the endoscope. When the device is mounted to an endoscope 18, a sheath 16 containing control wires and connected to the distal portion, extends parallel to the endoscope shaft, proximally to a control handle 14 as shown in FIGS. 1A and 1B.

Figure 3:
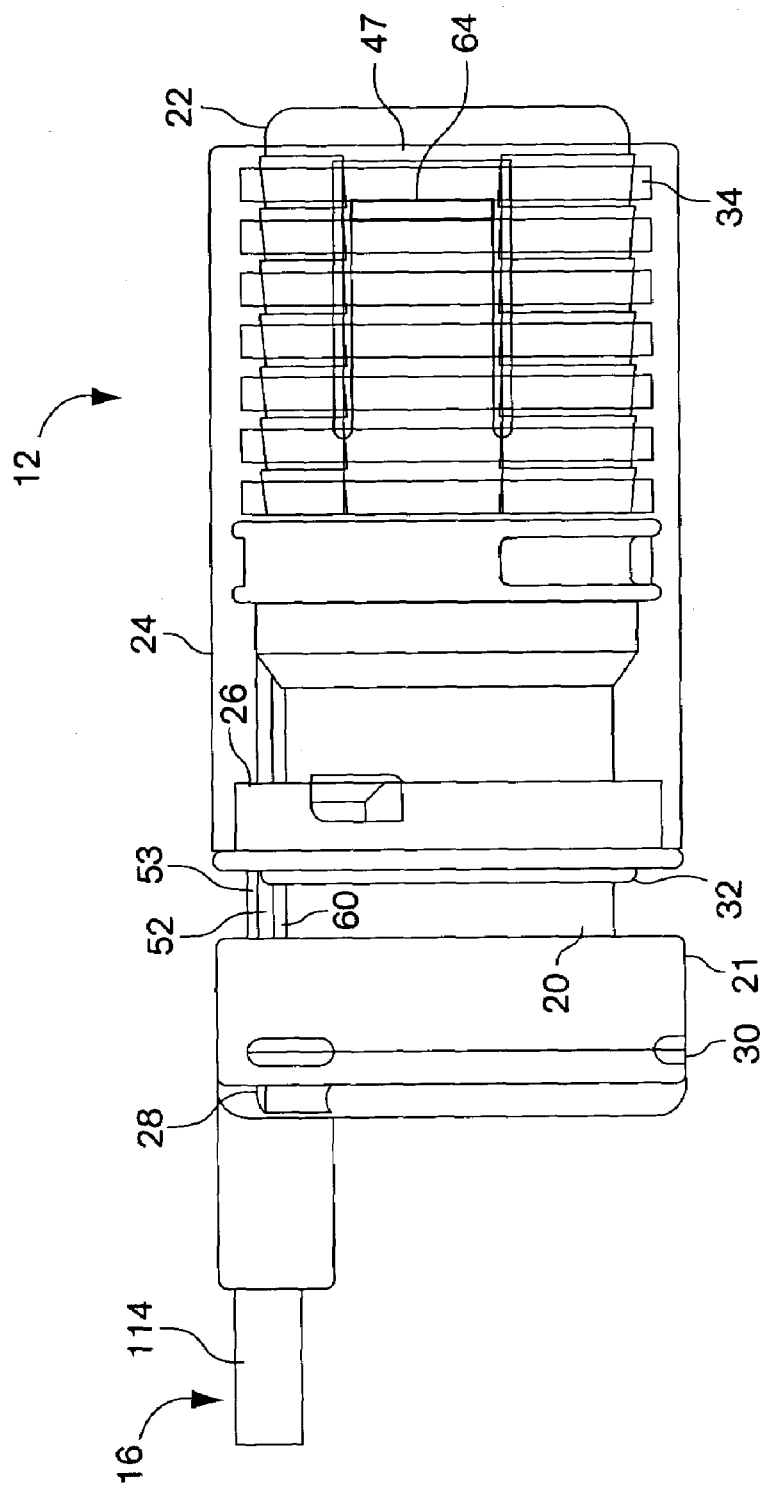
FIG. 3 is a side view of the distal portion of the band ligator.
Figure 4:
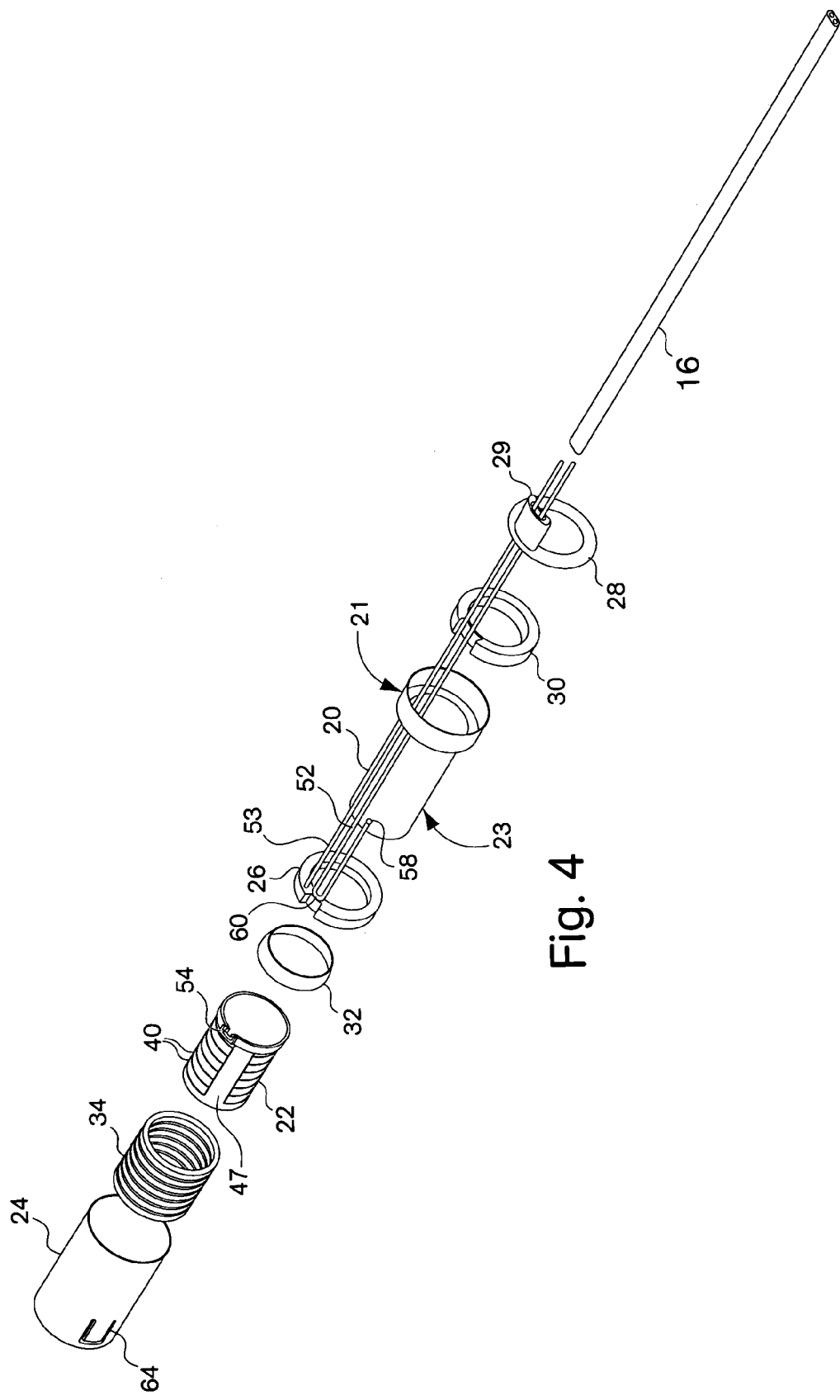
FIG. 4 is an exploded view of the components of the distal portion of the band ligator.

FIG. 3 shows an assembly drawing of the distal portion 12 of the ligating device. An exploded view of the distal portion of the device revealing its individual components is shown in FIG. 4. The distal portion 12 is comprised of three coaxially arranged tubes: a static sleeve 20 (inner most tube); a band carrier 22 (middle tube) and; a band driver 24 (outer tube). Operation of the device involves relative sliding movement of the tubes to effect band delivery.

Figure 5:
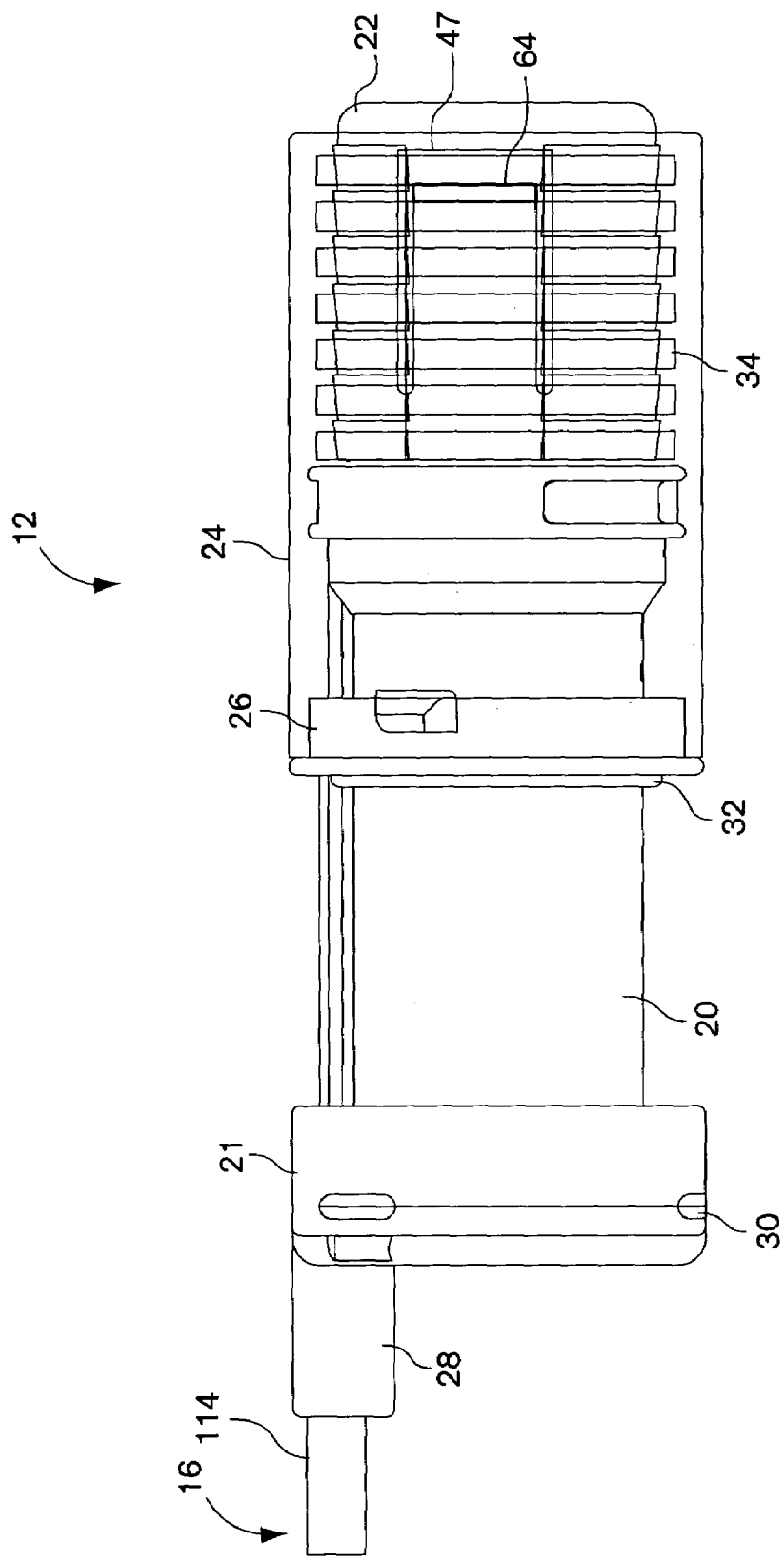
FIG. 5 is a side view of the distal portion of the band ligator with the band carrier and band driver in an extended position relative to the static sleeve.
Figure 6:
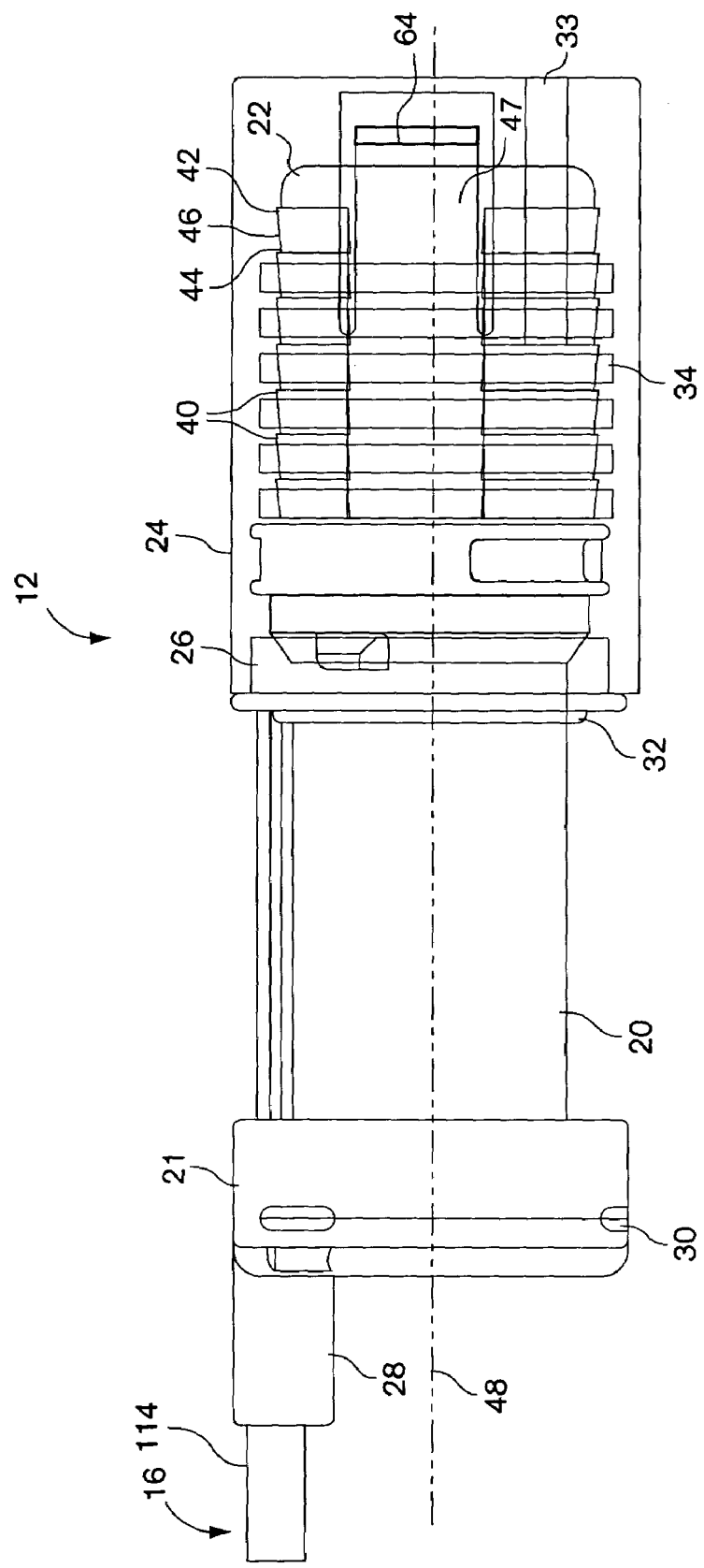
FIG. 6 is a side view of the distal portion of the band ligator with the band carrier extended relative to the static sleeve and the band driver extended relative to the band carrier to discharge a band.

When the device is navigated to a tissue treatment site such as a varix location, the tubes are in a retracted position, such that the band driver 24 and band carrier 22 are positioned proximally on the static sleeve 20. In this position the distal portion 12 does not interfere with the peripheral view through the viewing lens 11 on the distal face 15 of the endoscope (FIGS. 2B and 3). When the varix site has been reached, the band driver 24 and band carrier 22 together are slid distally relative to static sleeve 20 to the position shown in FIG. 5. By their distal movement on the static sleeve, the band carrier 22 and band driver 24 together are extended beyond the distal face of the endoscope. The cylindrical interior of the band carrier creates a vacuum chamber, closed at its proximal end by the endoscope distal face 15 and open at its distal end to receive tissue. Band carrier 22 and driver 24 are preferably made from transparent polymer materials to minimize interference with peripheral viewing through the endoscope when they are advanced beyond the distal face 15. Tissue is aspirated into the vacuum chamber when suction is applied through the vacuum port 13 on the distal face of the endoscope. With the tissue aspirated into the suction chamber, the band driver 24 is then slid distally relative to the band carrier 22 to push a band 34 from the band carrier and onto the tissue (FIG. 6).

The exploded view of the distal portion 12 presented in FIG. 4 shows the arrangement of components that permit the operation described above. The static sleeve 20 is the innermost tube and serves as a base member for the assembly of all components that comprise the distal portion of the device. The static sleeve has a small diameter portion 23 that steps up to a large diameter portion 21 at the proximal end of the sleeve. The inner diameter of the small diameter portion 23 is sized to closely fit the largest commercially available endoscope size. For smaller endoscopes, an adapter, which is discussed below, may be used to provide a snug fit. To help ensure proper longitudinal positioning of the ligator on the endoscope shaft, at the distal tip 27 of the static sleeve 20 may be formed a small radially inward projecting lip sufficiently deep to catch the distal face of an endoscope inserted therein. The lip serves as a stop to align the distal face of the endoscope with the distal end 27 of the static sleeve Fitted into the large proximal portion 21 is an annular vacuum seal 30. A proximal retainer 28 is snap-fit into the enlarged diameter proximal portion 21, capturing the vacuum seal 30 in the assembly. The vacuum seal helps to provide a vacuum tight friction fit for the device onto an endoscope shaft that helps to promote greater suction in the vacuum chamber when the band carrier is extended and vacuum applied. The sheath 16, which houses control wires that lead to the proximally located handle, terminates and is fixed in receptacle 29 of the proximal retainer 28.

Figure 7A:
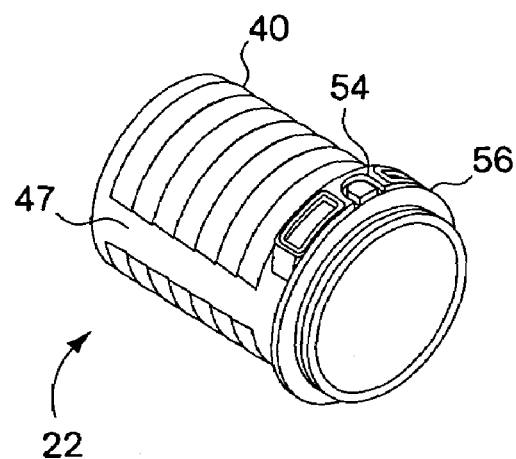
FIG. 7A is an isometric view of the band carrier.
Figure 7B:
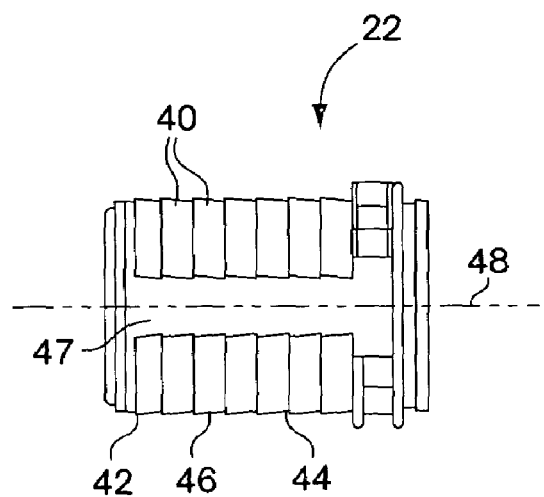
FIG. 7B is a side view of the band carrier.

A cylindrical band carrier 22, shown in detail in FIGS. 7A and B, is slidably mounted on the static sleeve 20. The band carrier has a plurality of circumferential sawtooth ridges 40 extending along its length configured to carry seven ligating bands in readiness for delivery. The distal side 42 of each ridge 40 is of a greater diameter than the proximal side 44 of each ridge. The land 46 between the proximal and distal ends of each ridge is angled away from the longitudinal axis 48 of the band carrier, extending radially inward as it extends in the proximal direction. The land area of each ridge is approximately 0.075 inch in length, which is slightly greater than the thickness of a stretched ligating band (0.075 inch nominal thickness—unstretched), which will be carried on each land area. There are seven ridges and corresponding land areas configured to carry the seven bands. It is noted that the device can be configured to carry any number of ligating bands, or just a single band, and the configuration for seven bands is meant merely to be exemplary for a multiple band ligator.

The sawtooth arrangement of the ridges helps to prevent unintended longitudinal movement of the bands on the band carrier surface. The diameter increase between the proximal side 44 of a given ridge and the distal side 42 of the next proximally adjacent ridge provides a small backstop that holds the bands from sliding proximally when they engage surfaces of the proximally moving band driver as will be discussed below. Also, the ridges provide a slight gap between bands that facilitates engagement with the driving surfaces of the resilient fingers 64 of the band driver 24.

Through the ridges 40 are formed two smooth surface channels 47 extending longitudinally along the band carrier, 180° apart. The surface of the channels is smooth and free from the elevated ridges 40 that make up the remaining circumferential area of the band carrier. The channels are intended to align with the resilient arms 64 of the coaxially arranged band driver 24 so that the ribs 40 do not engage the arms 64 to interfere with the smooth longitudinal movement of the driver 24 over the carrier 22.

Vacuum seal ring 32 is positioned between the outer surface of the static sleeve 20 and the interior surface of the band carrier 22. The presence of the vacuum seal ring between those two cylinders helps to insure that sufficient suction is developed in the vacuum chamber created when the band carrier 22 is slid distally relative to the static sleeve 20 and beyond the distal face 15 of the endoscope to capture tissue.

The band carrier 22 and band driver 24 together may be moved longitudinally relative to the static sleeve 20 by movement of the static control wire 52 distally relative to the sheath 16. The static wire 52 wraps around and is held fixed in U-shaped receptacle 54 formed in rib 56 at the proximal end of the band carrier. As the control wire extends through the U-shaped receptacle, one side of the wire extends proximally back through the sheath 16 to the control handle 14 of the device. The end of the control wire extending through the other side of the U-shaped channel continues proximally slightly to provide an extension 60 that terminates in a ball tip 58. The extension 60 slides through a passage in the static sleeve and proximal retainer 28 large enough for only the wire to pass, but not the ball tip. When the ball tip reaches the passage (not shown), it stops the longitudinal travel of the wire in the distal direction. The remaining length of wire 60 and ball tip 58 correspond in length to the amount of longitudinal travel that the band carrier 22 can have on the static sleeve 20 without becoming disconnected. Thus, the remaining portion of the wire 60 and ball stop 58 comprise a safety limit stop that prevents the band carrier from being overextended during use.

Figure 8A:
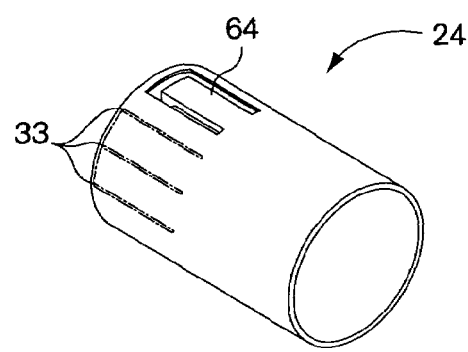
FIG. 8A is an isometric view of the band driver.
Figure 8B:
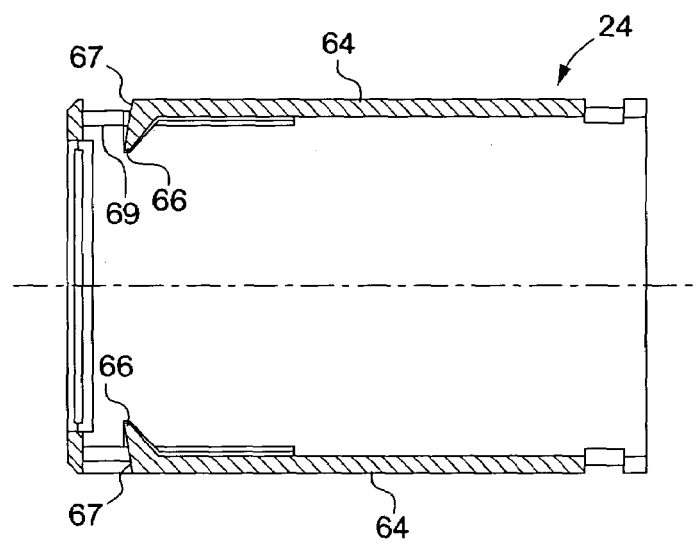
FIG. 8B is a sectional view of the band driver.

The band driver 24 is slidably received over the band carrier with resilient arms 64 arranged to slide within diametrically opposed channels 47 as discussed above. Band driver retainer 26 is snap-fit into the proximal end of the band driver 24 and fixedly receives driver control wire 53 so that longitudinal movement of the driver relative to the band carrier 22 and static sleeve 20 can be affected from the proximally located handle. As shown in FIGS. 8A and 8B, the two resilient arms 64 each have pointed radially inward directed protrusions 66 with distal faces 67 that serve to engage the bands 34 mounted on the band carrier 22. Distal movement of the band driver 24 results in the distal faces 67 of protrusions 66 pushing the band off the carrier 22. A small amount of Dow Corning medical fluid (silicon) is used on the band carrier surface to provide lubricity and ease distal sliding of the bands during delivery.

Also, as shown in FIGS. 6 and 8A, to ensure smooth sliding motion of the band driver 24 over the band carrier 22, several longitudinally extending and radially spaced centering ribs 33 may be formed on the inside surface of the band driver. The ribs 33 take up slack between the inside diameter of the band driver and the outside diameter of the band carrier. The ribs ensure that the band driver remains concentric around the band carrier, preventing cocking that could hinder sliding movement. With a band driver formed from molded plastic, the ribs may be formed directly in or on the inside surface of the band driver. The ribs need not extend the entire length of the band driver and may be formed to taper down in height from the distal end to the middle of the driver.

After a band is pushed from the carrier, the band driver 24 is moved proximally back along the carrier such that the protrusions 66 and resilient arms 64 ride over the next most distal band and become lodged on the proximal side of the band in readiness to push the band distally with the next distal movement of the band driver. Proximal sliding of the band when the resilient arms pass over is prevented by the ridged surface of the band carrier.

Figure 8C:
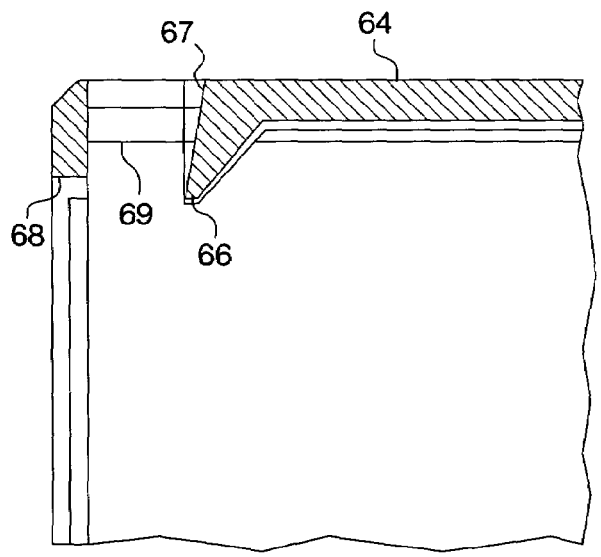
FIG. 8C is a detailed sectional view of the band driver.

The interior surface of the band driver is configured such that its distal edge 68 is of a reduced diameter that is smaller than the outside diameter of a band loaded onto the band carrier, as shown in FIG. 8C. Accordingly, although the resilient arm 64 can flex to permit protrusions 66 to ride over a band mounted on the band carrier during proximal sliding movement of the band driver, proximal movement of the driver relative to the carrier stops when a band abuts the distal edge 68 because the reduced diameter will not permit passage over the band. The band is prevented from sliding proximally under the force presented by the distal edge 68 by virtue of the saw-tooth ridges on the band carrier. After the band driver has delivered a band and is retracted proximally to position the driving faces 67 of the protrusions 66 behind the next band to be delivered, the distal edge 68 will butt up against the distal side of that band preventing further proximal movement of the band driver relative to the band carrier. Between the distal edge 68 and driving face 67 is defined a band receptacle area 69 in which a single band loaded onto the carrier fits. Because the most distal band will be confined to the receptacle area 69 of the band driver during advancement off of the band carrier, the receptacle area ensures that only one band is delivered at a time.

Handle Configuration—Generally

Figure 9:
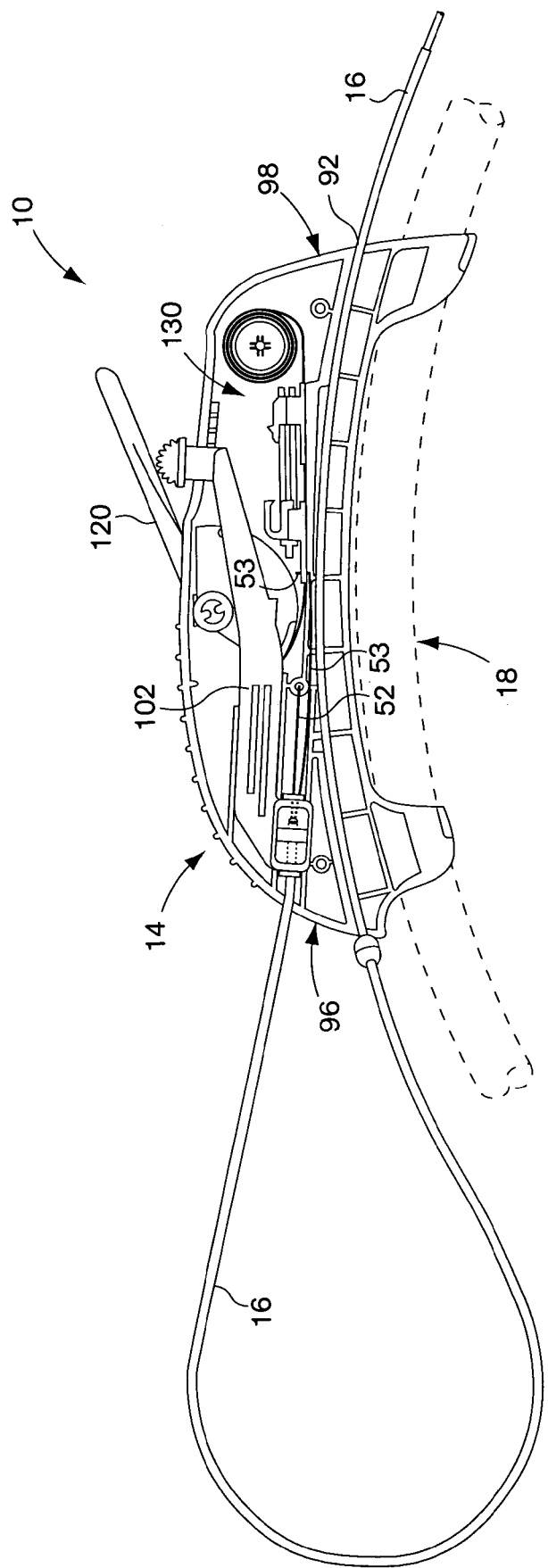
FIG. 9 is a sectional view of the control handle mounted on an endoscope (shown in phantom)

Extending proximally from the band ligator distal portion 12 described above is a control sheath 16 containing static wire 52 and driver wire 53 all joined to control handle 14, as shown in FIG. 9. Slide 102 and thumb lever 120, mounted externally on the control handle 14, are operated to move static wire 52 and driver wire 53 relative to the sheath 16 to cause corresponding relative movement between the static sleeve, band carrier and band driver to deliver ligating bands as described above. The handle 14 is configured to be releasably and slidably mounted onto an endoscope shaft 18 (shown in phantom) and is sized to permit an operator to simultaneously grasp and control both the handle and mid-portion of the endoscope shaft with one hand.

Figure 10B:
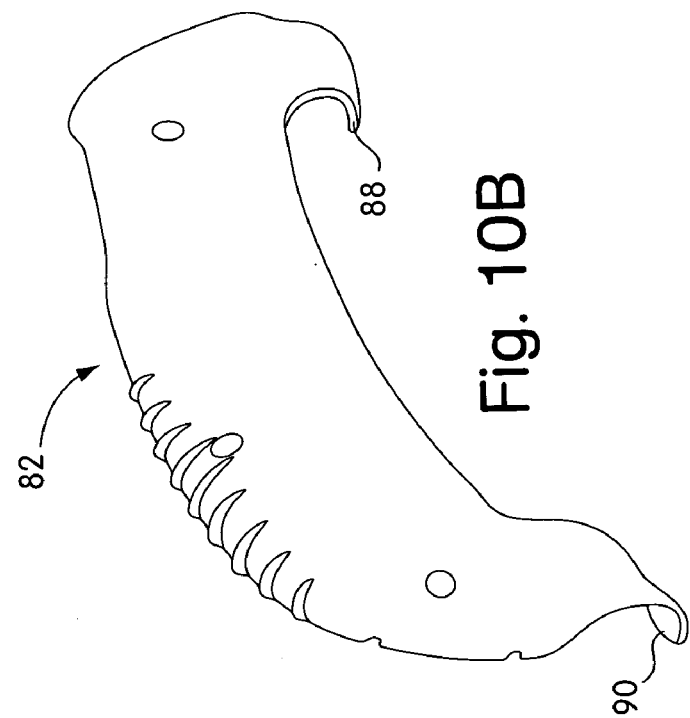
FIGS. 10A and 10B are isometric illustrations of left and right body halves of the control handle assembly.
Figure 10A:
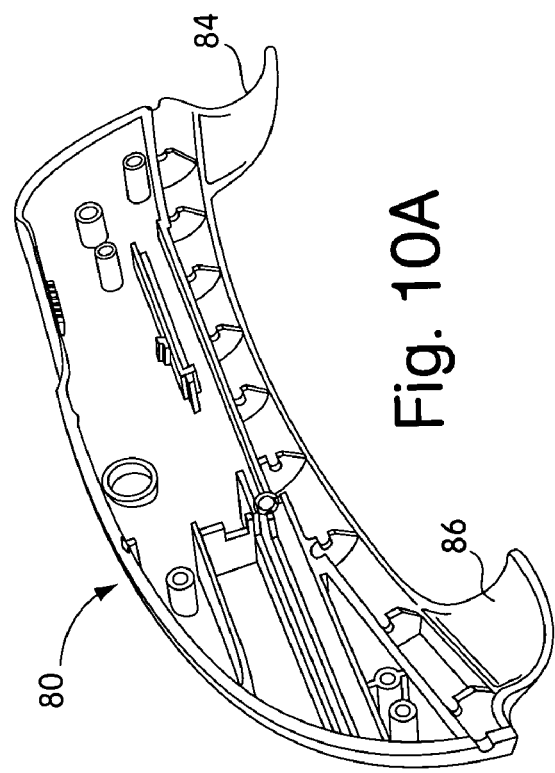

The control handle 14 is formed from two molded plastic body halves 80 and 82 shown in FIGS. 10A and 10B. The left body half 80 is shown with handle components assembled in FIG. 9. The assembled handle is slidably and releasably retained on an endoscope shaft 18 by the serpentine arrangement of curved forks 84, 86, 88 and 90 that extend from the body halves to loosely surround the endoscope shaft. When the body halves are assembled, the forks are staggered longitudinally but curve downwardly and around to overlap and define a circumferential pathway that guides the shaft at the bottom of the handle along its entire length. Still, the forks are staggered sufficiently to permit passage of the shaft when it is angled away from the longitudinal axis of the handle to slip past the fork tips. With the serpentine arrangement of the forks, the handle can be applied to or removed from the endoscope shaft laterally, without requiring removal of end components of the endoscope so that the handle can be slipped off the end.

Once mounted, the handle 14 can be slid longitudinally along the scope shaft 18 with the physician's right-hand or temporarily restrained in position by grasping the endoscope and handle together between the curved forks. As the handle is slid longitudinally along the endoscope, the sheath 16 freely slides through the sheath channel 92 formed through the body of the handle in order to accommodate the corresponding change in distance between the handle and the distal portion 12 of the band ligator. To maintain smooth device operation through the sheath while maintaining free length adjustability, the proximal end 94 of the sheath, joined to the manipulation controls, is arranged to exit the handle proximal end 96. The sheath then forms a loop 99, reversing its direction, and reenters the handle through the sheath channel 92. The sheath is slidably received through sheath channel 92 and exits the distal end 98 of the handle and continues distally, outside of the endoscope, to its connection to the distal portion 12 of the band ligator.

The reverse loop configuration prevents bowing of the sheath 16 in the area between the handle and the distal portion 12 of the device, which could cause interference in operating the control wires 53 and 52 through the sheath as well as cause interference in the smooth longitudinal movement of the handle along the endoscope. Instead, as the handle moves longitudinally along the endoscope, sheath 16 slides though sheath channel 92, and the size of the loop 99 changes to accommodate the change in distance between handle and distal portion 12. The size of the loop at the proximal side 96 of handle does not interfere with movement of the handle along the endoscope nor does it interfere with the operation of the control wires as the sheath is not forced to bow at the critical area of the proximal end 94, immediately adjacent to its attachment to the control mechanisms. A stop 101 is fixed to the exterior of the sheath to prevent it from being fed too far into the sheath channel 92 such that the curvature of the loop 99 becomes excessively tight, possibly impairing operation of the control wires.

Figure 11A:
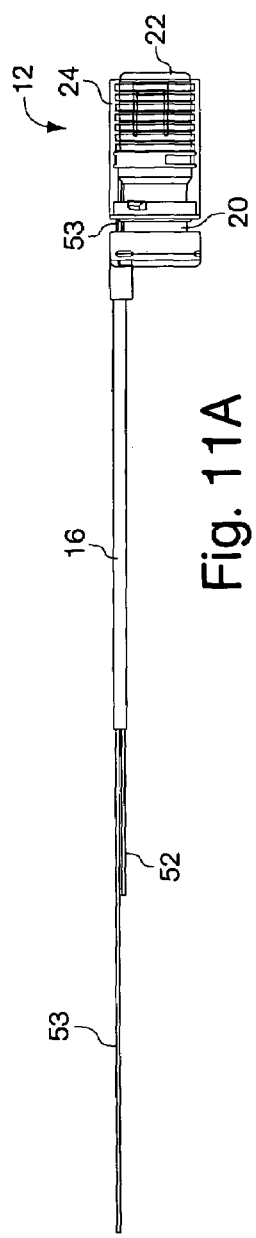
FIGS. 11A–11C are side view illustrations of the several stages of operation of the distal portion of the band ligator.
Figure 11B:
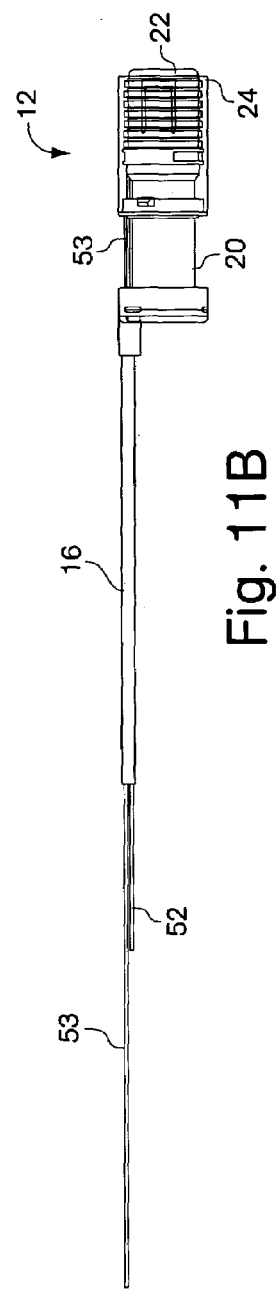
Figure 11C:
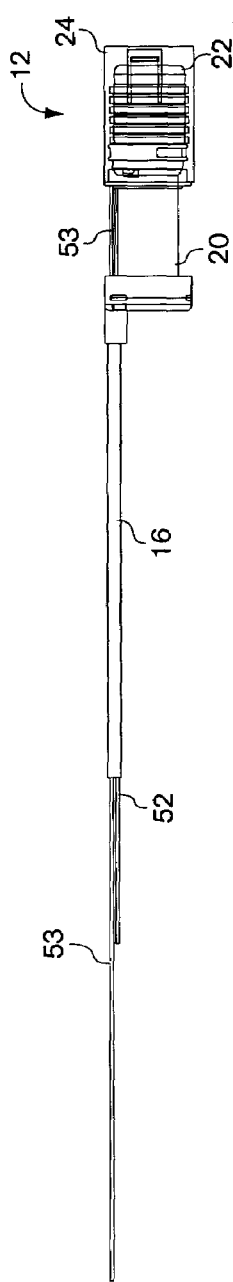
Figure 12A:
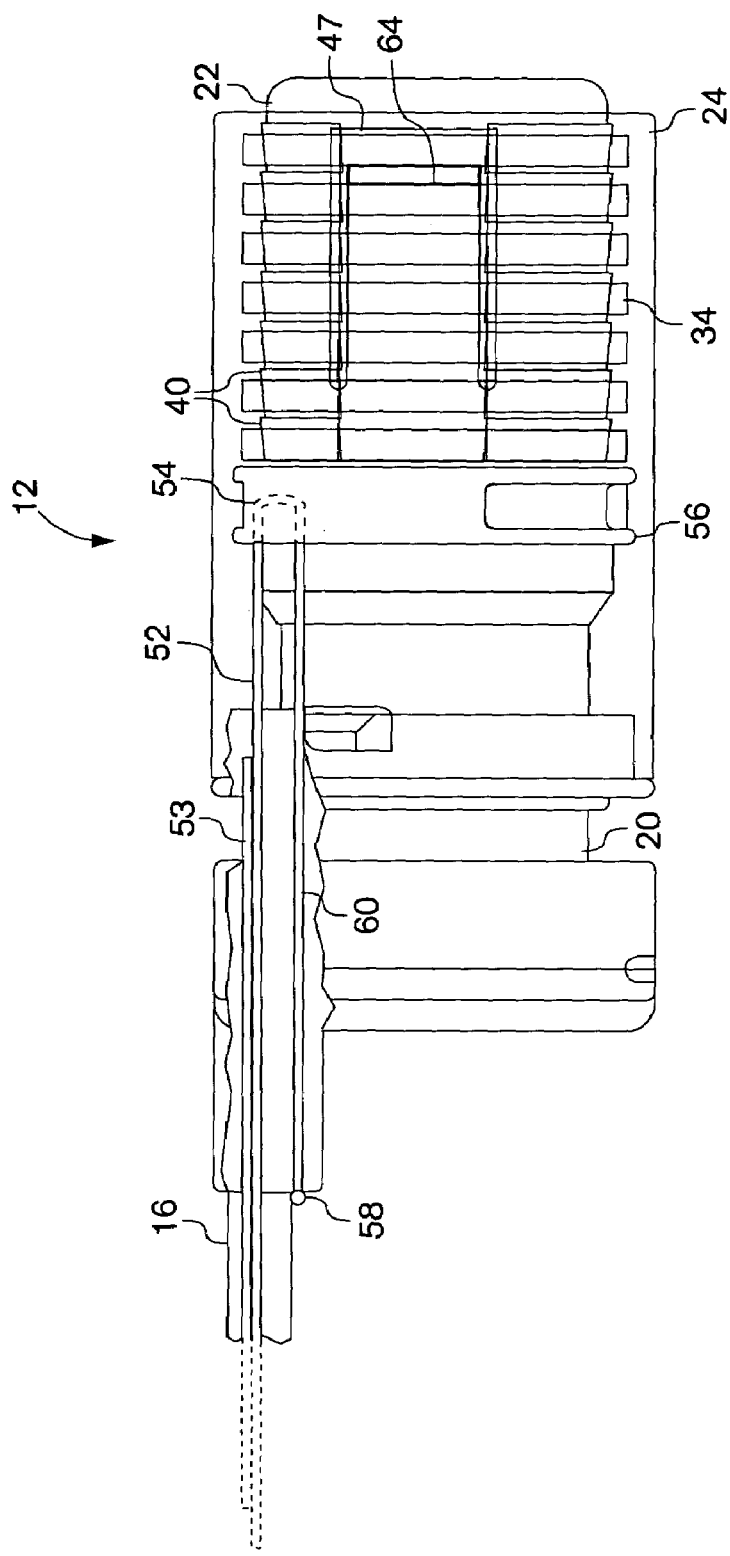
FIGS. 12A–12C are partial sectional side view illustrations of the distal portion of the band ligator in various stages of operation.
Figure 12B:
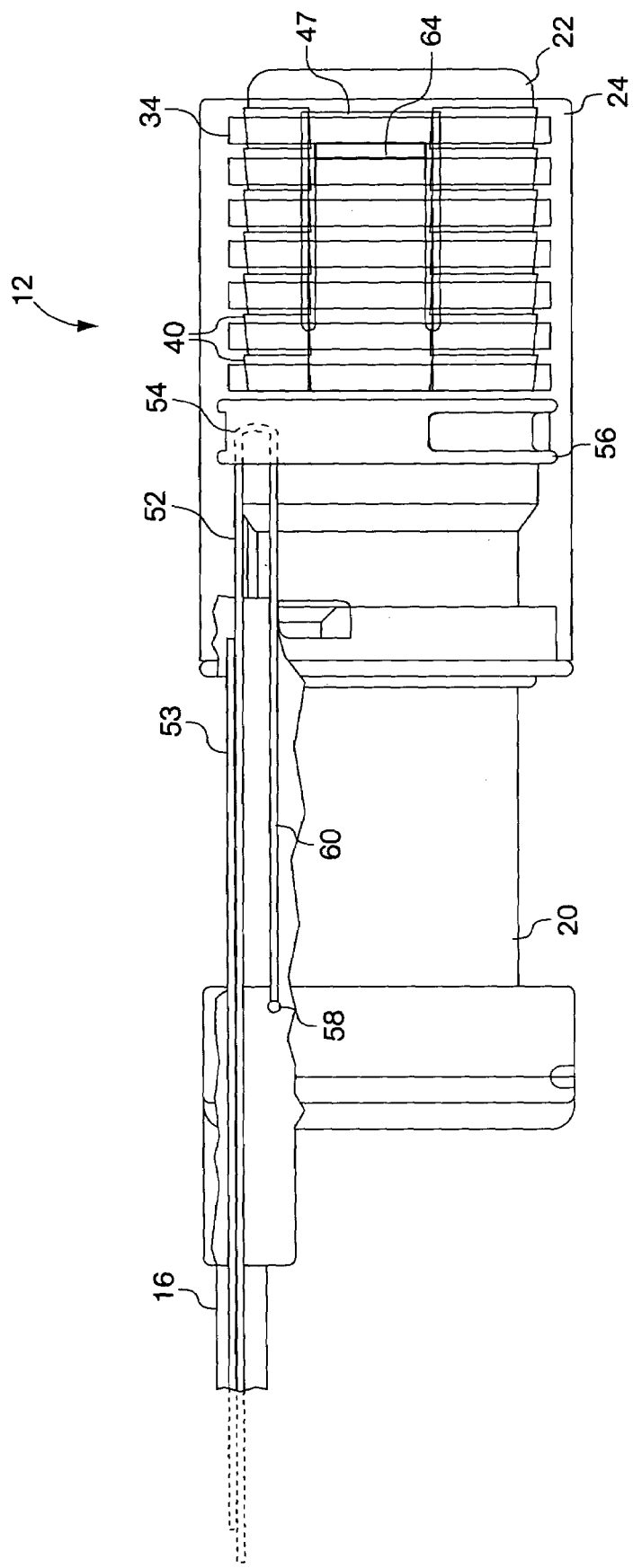
Figure 12C:
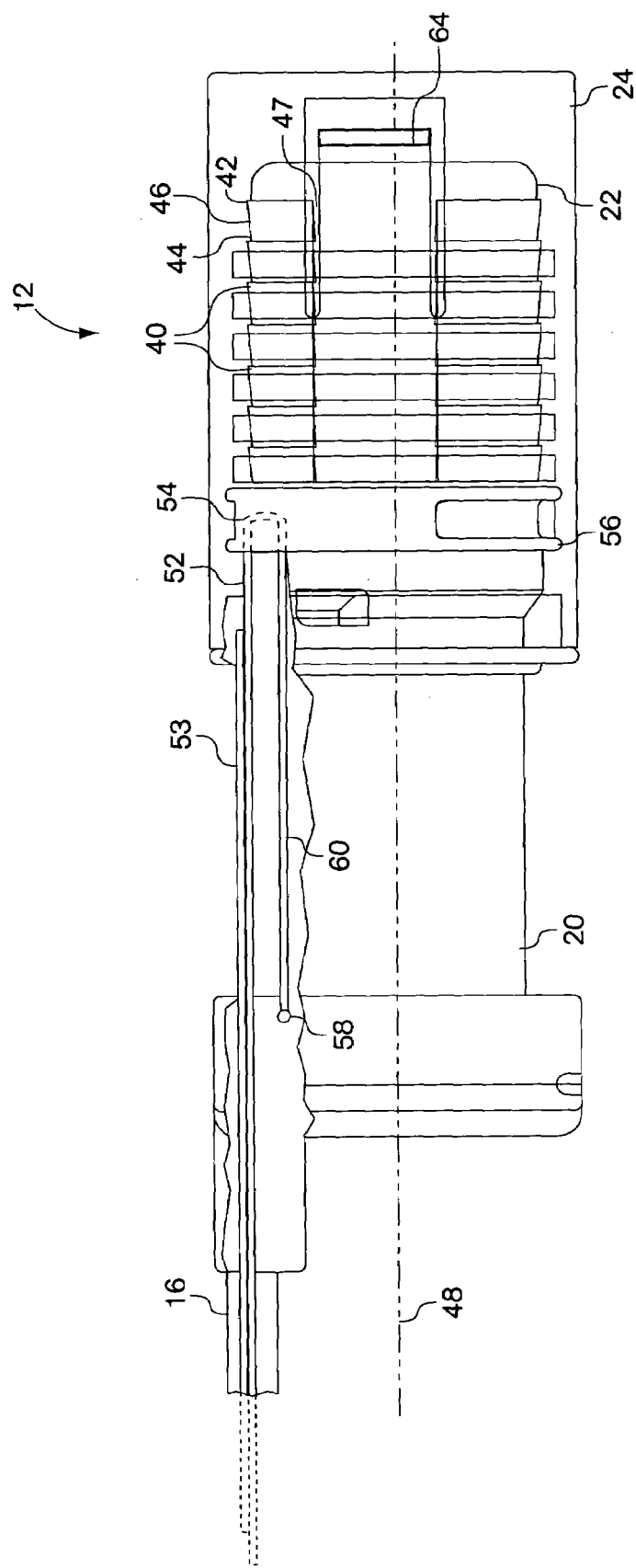

The handle controls, slide 102 and lever 120, operate to slide control wires 52 and 53 relative to sheath 16 to move the components of distal portion 12 through their various positions shown in FIGS. 11A–11C and 12A–12C. Additionally, certain surfaces of the handle, slide and lever assemblies serve as limit stops and safety lockouts to ensure that the controls cannot be moved out of sequence, preventing accidental release of a band. The details regarding the structure and operation of the slide and lever assemblies and the corresponding operation of the distal portion 12 is presented below in connection with FIGS. 12A–C showing the advancement steps of distal portion 12, FIGS. 13A and B showing a detailed view of the slide assembly and FIGS. 14A and B showing a detailed view of the lever and associated components.

Handle—Slide Movement for Band Carrier Advancement

In operation of the ligating device, the distal portion 12 is mounted on the distal end of an endoscope and the assembly advanced through the patient's mouth and into the esophagus. During navigation to the treatment area, the band carrier 22 and band driver 24 are both positioned proximally relative to static sleeve 20 as shown in FIG. 12A to minimize their extension beyond the distal face 15 of the endoscope so that viewing capability is preserved and the inflexible length presented by the ligator is minimized.

On the handle, slide 102 is maintained in its retracted position with thumb button 108 locked on the proximal side 104 of the slide detent 111, as shown in FIG. 13A, in order to maintain the band carrier and band driver proximally on static sleeve. The slide 102 controls longitudinal movement of the band carrier and driver on the static sleeve by controlling relative movement between the sheath 16 and the control wires 52 and 53. The proximal end 94 of the sheath is fixed to the slide 102 at receptacle 110 and the distal end 114 of the sheath is fixed to the static sleeve 20 (shown in FIGS. 12A–C). Static wire 52 is fixed at its proximal end to the left handle body 80 at boss 112 and at its distal end to the band carrier 22, slidable on the static sleeve. When the slide 102 is moved, the proximal end of the sheath is moved relative to static wire 52. Relative movement of the sheath and wire causes the band carrier to slide relative to the static sleeve 20. Band driver 24 remains synchronized with band carrier 22 during movement of the slide 102 by virtue of the band driver's positioning around the distal most band 34 on band carrier.

Viewing the handle in FIG. 13A, with the slide in the retracted (proximal) position, sheath is pushed distally on the static wire 52 (and driver wire 53). At the distal portion 12 of the ligator, as seen in corresponding FIG. 12A, wires 52 and 53 are withdrawn into sheath, which serves to maintain band carrier 22 and driver 24 in their proximal most position on static sleeve 20.

Relative movement between sheath and control wires is achieved, in part, by the connection of proximal end 94 of sheath 16 to the receptacle 110 of slide 102. The receptacle holds the sheath in fixed relation to the slide but permits the wires 52 and 53 to freely pass through. The receptacle may additionally contain coil springs (not shown) on each side of the sheath mounting location. The spring-loaded mounting of the sheath in receptacle 110 serves to provide a more positive lockout feel to the user as the slide is set at its proximal and distal extents of travel. The sheath and static wire 52 have comparative lengths such that as the band carrier reaches it proximal or distal extent, the slide must be moved longitudinally slightly more in order to reach its detent lock out position. That extra movement of the slide, after relative movement between the static wire and sheath has stopped, serves to compress one of the springs in the receptacle to achieve the final amount of travel of the slide. The firm engagement of the distal portion components against their limit stops and compression of the spring provides a connected feel to the operator.

In use, after a varix location has been identified visually through the endoscope, the distal end of the endoscope is steered to bring the distal face 15 and distal portion 12 of the ligator in close proximity to the varix. Next, band carrier 22 and band driver 24 are advanced distally, in unison, relative to the static sleeve 20 and endoscope shaft so that a cylindrical suction chamber is created inside the band carrier when it is advanced past the distal face of the endoscope as shown in FIG. 12B. When suction is applied through vacuum port 11 on distal face 15 of scope, the tissue area of the varix is drawn into the suction chamber so that a band can be slid onto the gathered tissue.

Figure 13B:
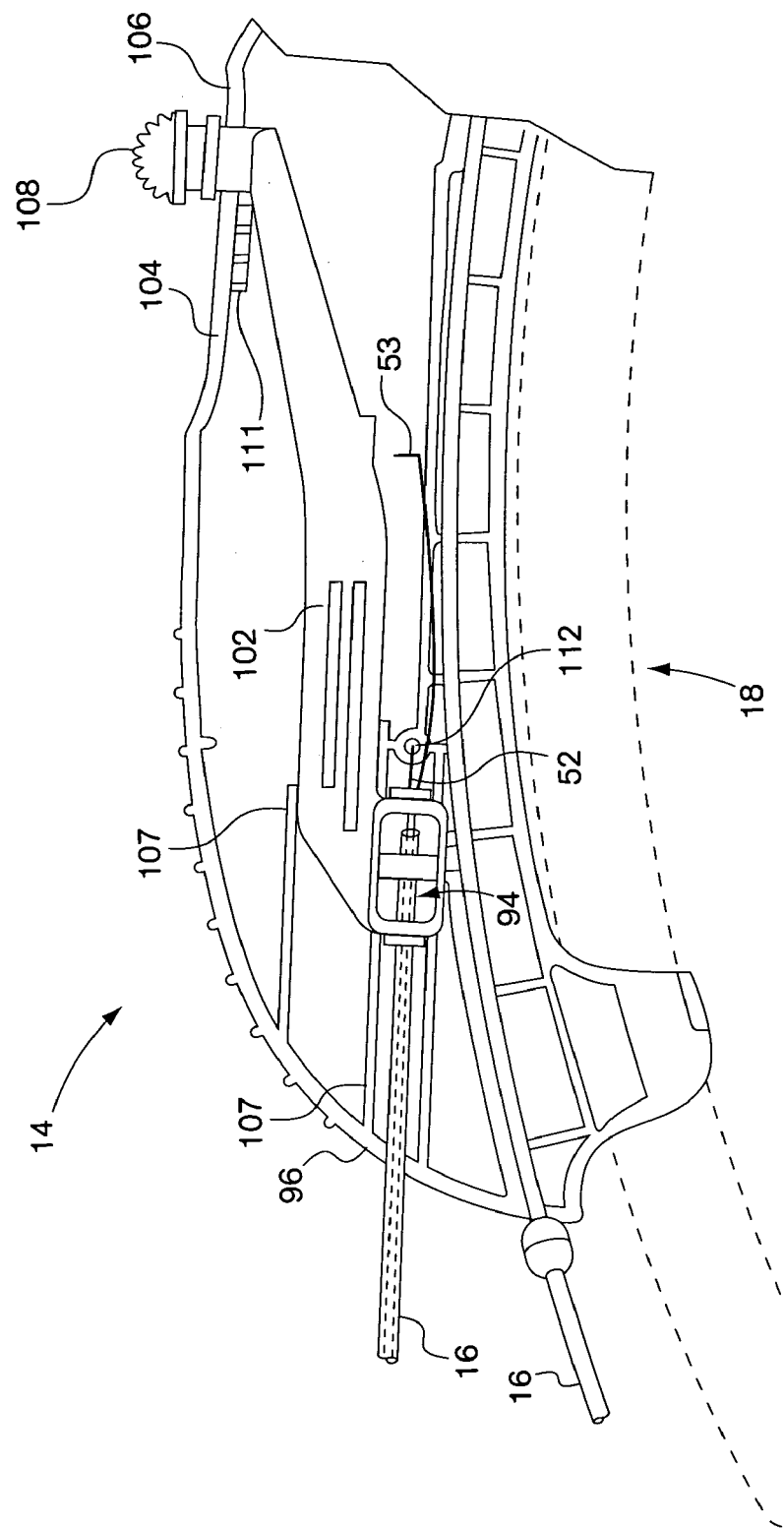

From the control handle, the advancement of the carrier and driver distally on the static sleeve 20 is achieved by moving the slide 102 from its retracted (proximal) position 104 to its advanced (distal) position 106, as shown in FIG. 13B. The user operates the slide by depressing the thumb button 108 to release slide from detent 111, moving slide forward and releasing the thumb button in the distal, locked position 106. The slide is slidable within a track defined by vanes 107 molded in the internal surfaces of the handle body halves 80 and 82. Movement of the slide distally, pulls the sheath into the handle, sliding it proximally relative to wires 52 and 53 (slide and sheath move to the right, as seen in FIG. 13B). As sheath 16 is pulled proximally relative to the static wire 52 at the handle, at the distal portion 12, the wire 52 is caused to project distally from the sheath 16, causing the band carrier 22 to be pushed distally relative to static sleeve 20 (as shown in FIG. 12B). Band driver 24 moves with band carrier when slide 102 is moved due to its engagement with band 34 as described above.

Handle—Lever Operation for Band Driver Advancement and Band Delivery

Figure 14A:
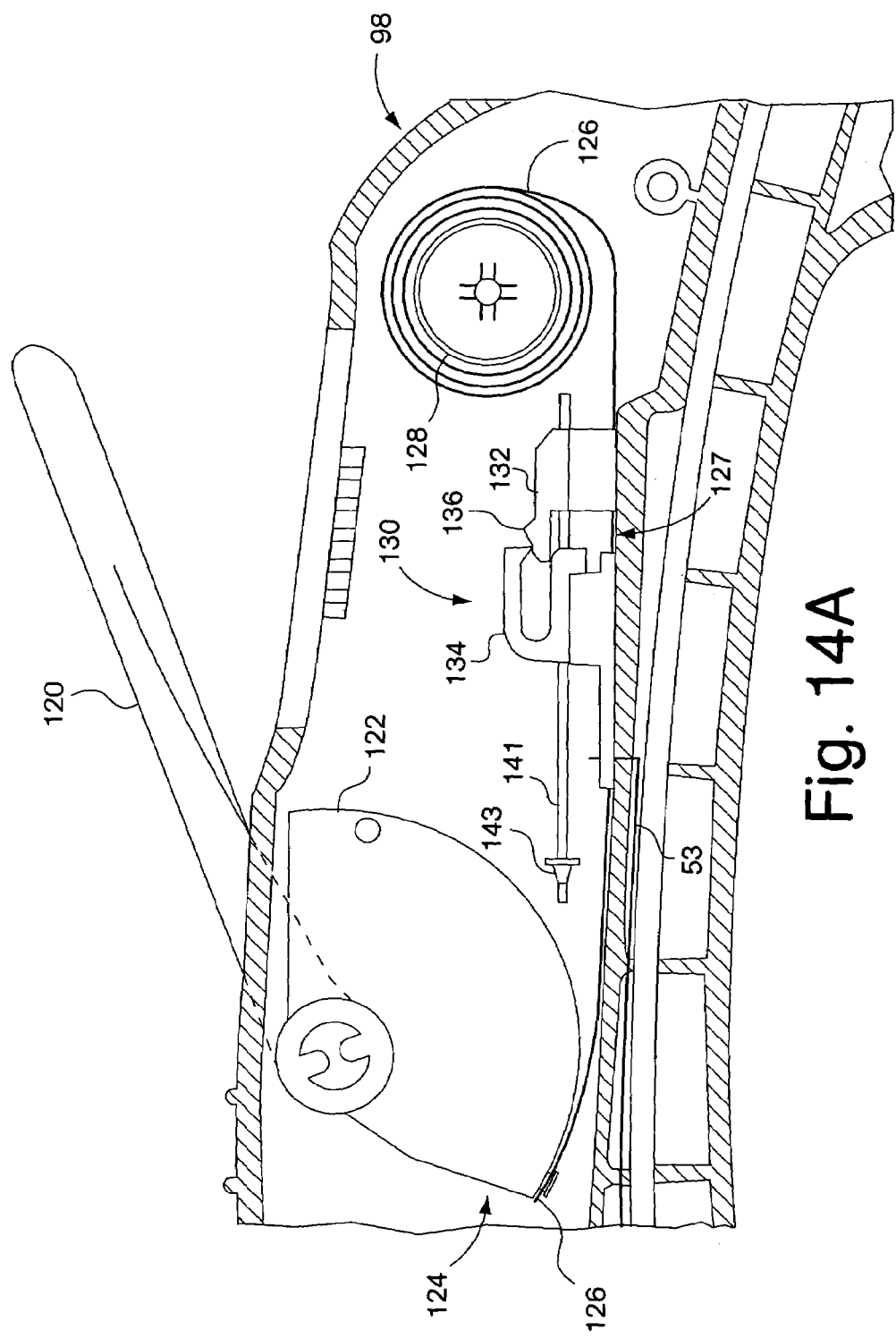
FIGS. 14A and 14B are a detailed sectional view of the control handle showing the thumb lever and associated components for operating the band driver.

After the band carrier 22 and band driver 24 have been advanced relative to the static sleeve 20 and the varix site aspirated into the suction chamber, the next step in operation of the device is to advance the band driver distally relative to the band carrier to discharge a band 34 as is shown in FIG. 12C. The band driver is moved longitudinally by operation of thumb lever 120 mounted to the side of the handle 14, as shown in FIGS. 9 and 14A & B. Depressing the lever 120 serves to advance the driver wire 53 distally through sheath 16 to push band driver 24 distally relative to the band carrier 22 so that resilient arms 64 push a band 34 from the device and onto the aspirated tissue. The handle is further configured so that when the lever 120 is released, the band driver 24 will automatically return proximally over the band carrier 22 to the extent necessary to place resilient arms 64 in position to move the next distal band 34. Advancement of and reliable automatic return of the band driver 24 is achieved by use of a return spring in combination with a releasable hitch arrangement to connect the lever 120 to the driver wire 53.

Detailed drawings of the lever 120 and associated components, with slide components deleted for clarity, are presented in FIGS. 14A and B. As seen in the figures, one end of the lever 120 protrudes from the handle 14 for operation by the user and the other end is connected inside the handle to a cam 122 that rotates when the lever is depressed. At the proximal side 124 of cam 122 is attached the end of a flat rolled return spring 126 that is collected onto a spool 128 near the distal end 98 of the handle. As the lever is depressed, the cam rotates and pulls the flat spring 126, unrolling it from the spool 128 to extend along pathway 127. When the lever 120 is released, the flat rolled spring 126 returns to its wrapped configuration around spool 128 pulling the cam 122 and lever to their original, undepressed position.

The driver wire 53 is joined to the return spring arrangement discussed above by a releasable hitch mechanism 130 arranged along the flat spring pathway 127 extending between its connection to the proximal end of cam 122 and the spring spool 128. The hitch assembly comprises two pieces: a tongue hitch 132 that is fixed to the unrolled portion of the flat spring between the cam and the spool and; a groove hitch 134 that is slidably mounted to the flat spring proximal to the tongue hitch. Both the tongue hitch and groove hitch are slidably received in a track 141 defined by vanes 139 molded in the internal surfaces of the handle body halves 80 and 82. To the groove hitch 134 is fixed the proximal end of driver wire 53. The tongue hitch 132 employs a tang 136 on the tongue portion that presents resistance whenever force is applied to cause the tongue to enter or be withdrawn from the groove of groove hitch 134. The tang provides a releasable frictional engagement between the tongue hitch and groove hitch as will be described below.

Figure 14B:
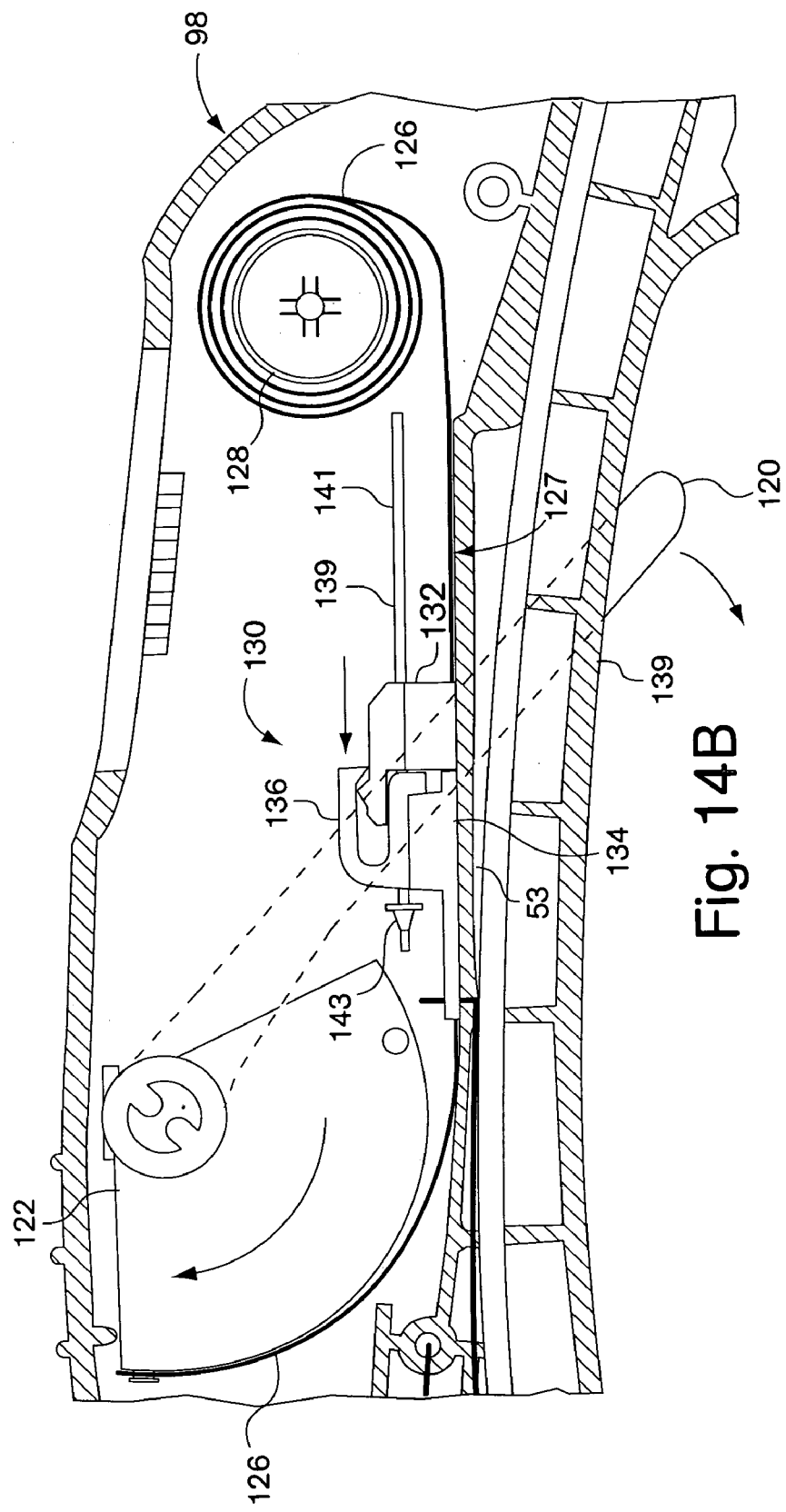

In the initial position of the band driver 24 shown in FIG. 12B, ready to discharge the first band 34, the lever 120 is undepressed as shown in FIG. 14A. Tongue hitch 132 and groove hitch 134 are positioned near their distal extents of travel, adjacent spool 128, but tongue is not fully engaged with the groove. When the lever 120 is depressed, cam 122 rotates to pull spring 126, thereby pulling tongue hitch 132 proximally as shown in FIG. 14B. By its unengaged abutment with groove hitch 134, the tongue hitch pushes the groove hitch proximally along track 141 to advance the driver wire 53 distally through the sheath (groove hitch 134 and tongue hitch 132 move to the left as shown in FIG. 14B). Tang 136 presents sufficient resistance during this movement to prevent the tongue hitch from entering groove hitch. Distal movement of the driver wire 53 serves to push the band driver 24 distally relative to the band carrier 22 as is shown in FIG. 11C.

As the user fully depresses the lever 120, the groove hitch 134 stops against abutment 143 molded into handle body at the proximal end of track 141. The resistance presented by tang 136 of the tongue hitch 132 is overcome and the tongue becomes engaged with the groove hitch 134 with an audible click that indicates to the user that the band driver has been extended to its maximum distal range of travel to deliver a band. When the operator releases the lever 120, the return spring 126 recoils around spool 128 rotating cam and lever back to their initial positions. The recoiling spring also draws with it tongue hitch 132 along with the now engaged groove hitch 134 (hitches 132 and 134 move to the right in back to their original positions shown in FIG. 14A). The distal movement of the groove hitch 132 serves to pull the driver wire 53 proximally relative to the sheath to return the band driver 24 proximally to a position in which the resilient fingers 64 are in position to deliver the next band.

The extent of proximal travel of the band driver 24 is determined by the abutment of the distal edge 68 of the band driver against the next distal band 34. As discussed above, the distal edge of the band driver is sufficiently undersized to prevent the driver from sliding proximally over the next distal band 34. The abutment of the distal edge with the next distal band in combination with the tensile force applied by the flat rolled spring is sufficient to overcome resistance offered by tang 136 causing tongue hitch 132 to disengage from groove hitch 134. Proximal sliding of the band when engaged by the distal edge is effectively resisted by the ridges formed on the band carrier. The hitch assembly 130 is then left in the position shown in FIG. 14A, in readiness to be operated again by lever 120 to deliver the next band.

Figure 15:
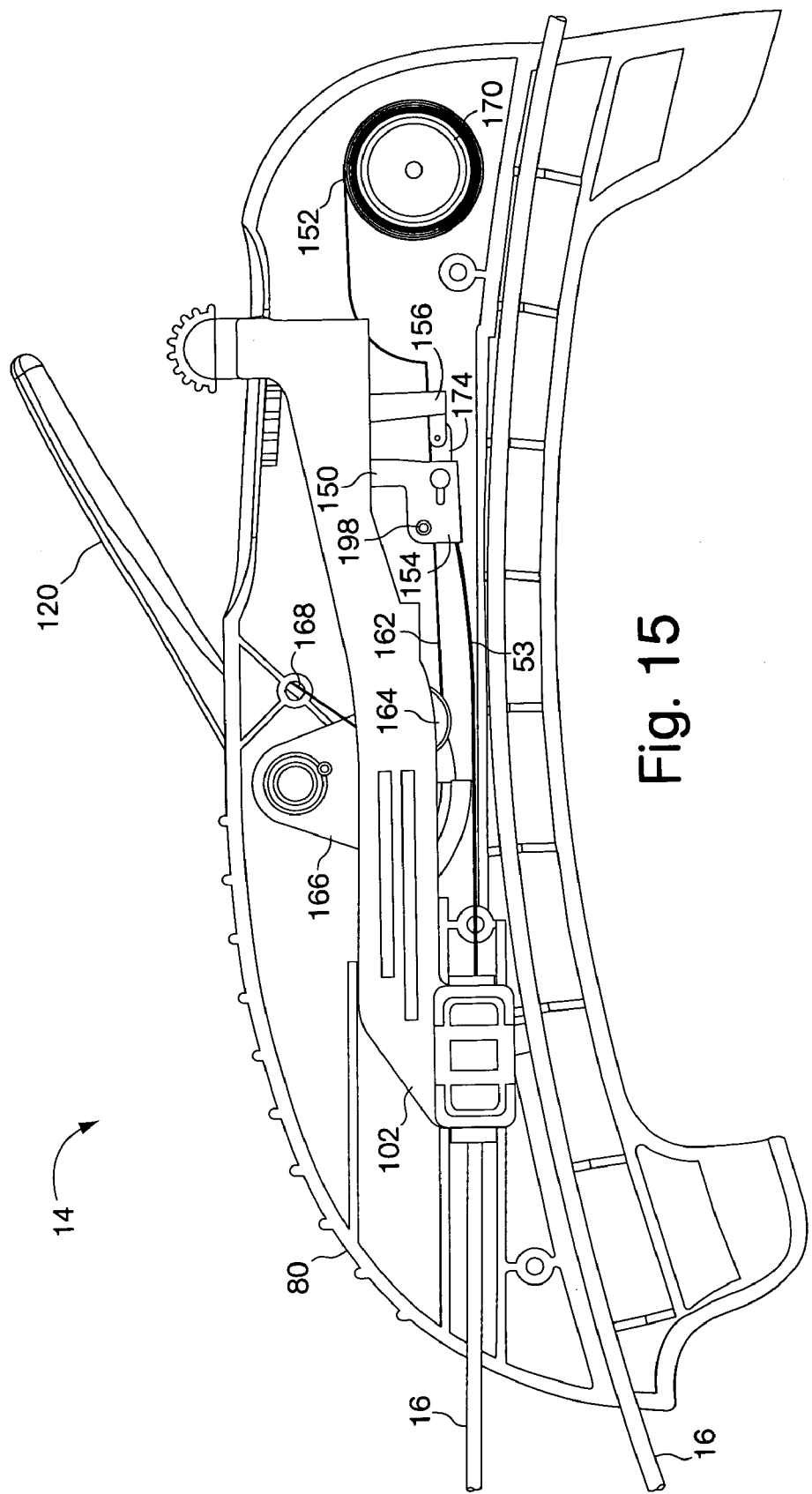
FIG. 15 is a detailed sectional view of the control handle showing components for operating the band driver according to a second embodiment of the invention.
Figure 16:
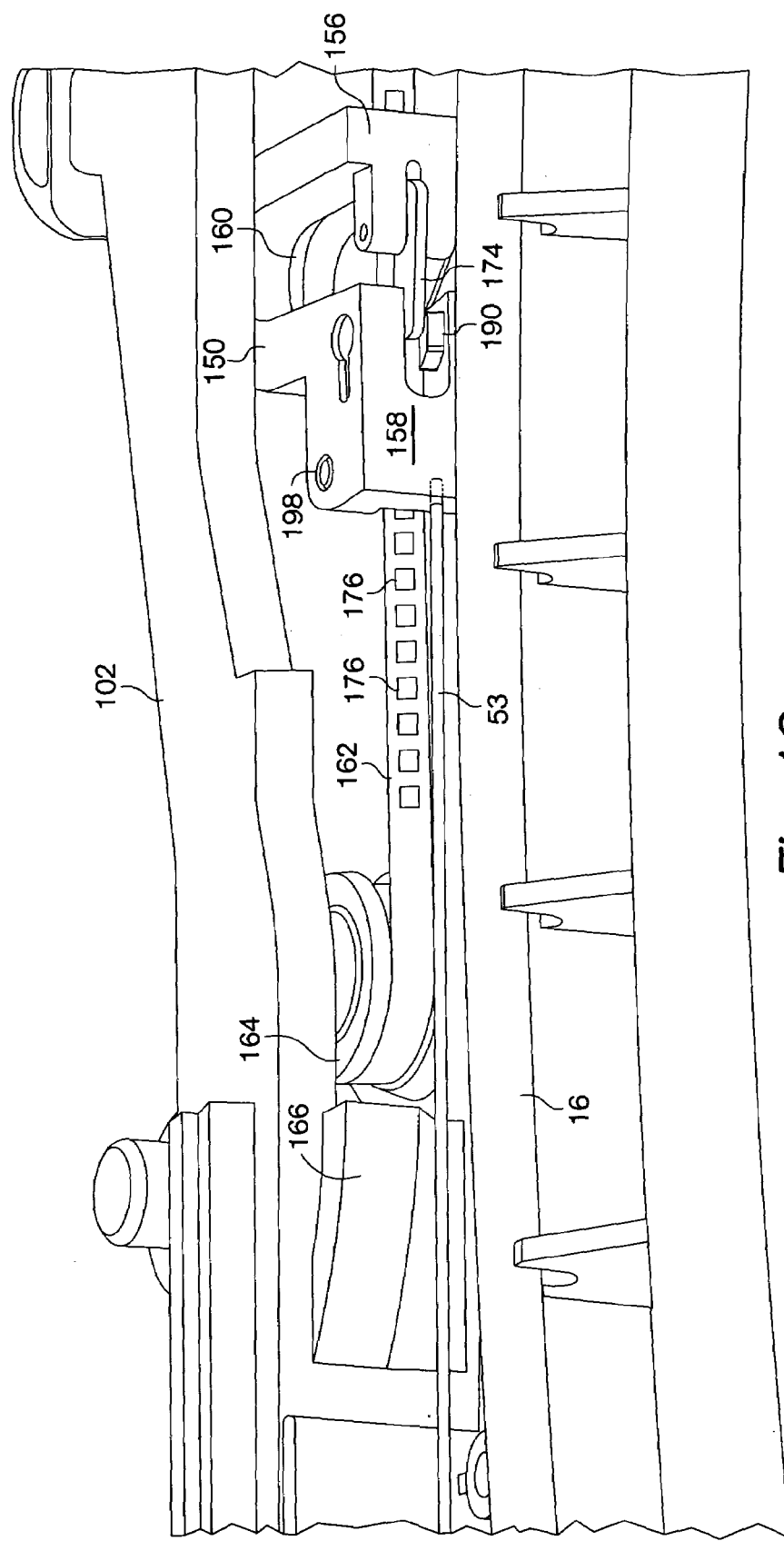
FIG. 16 is a bottom sectional view of the control handle detailing the configuration of the strap and flexible arch.
Figure 17:
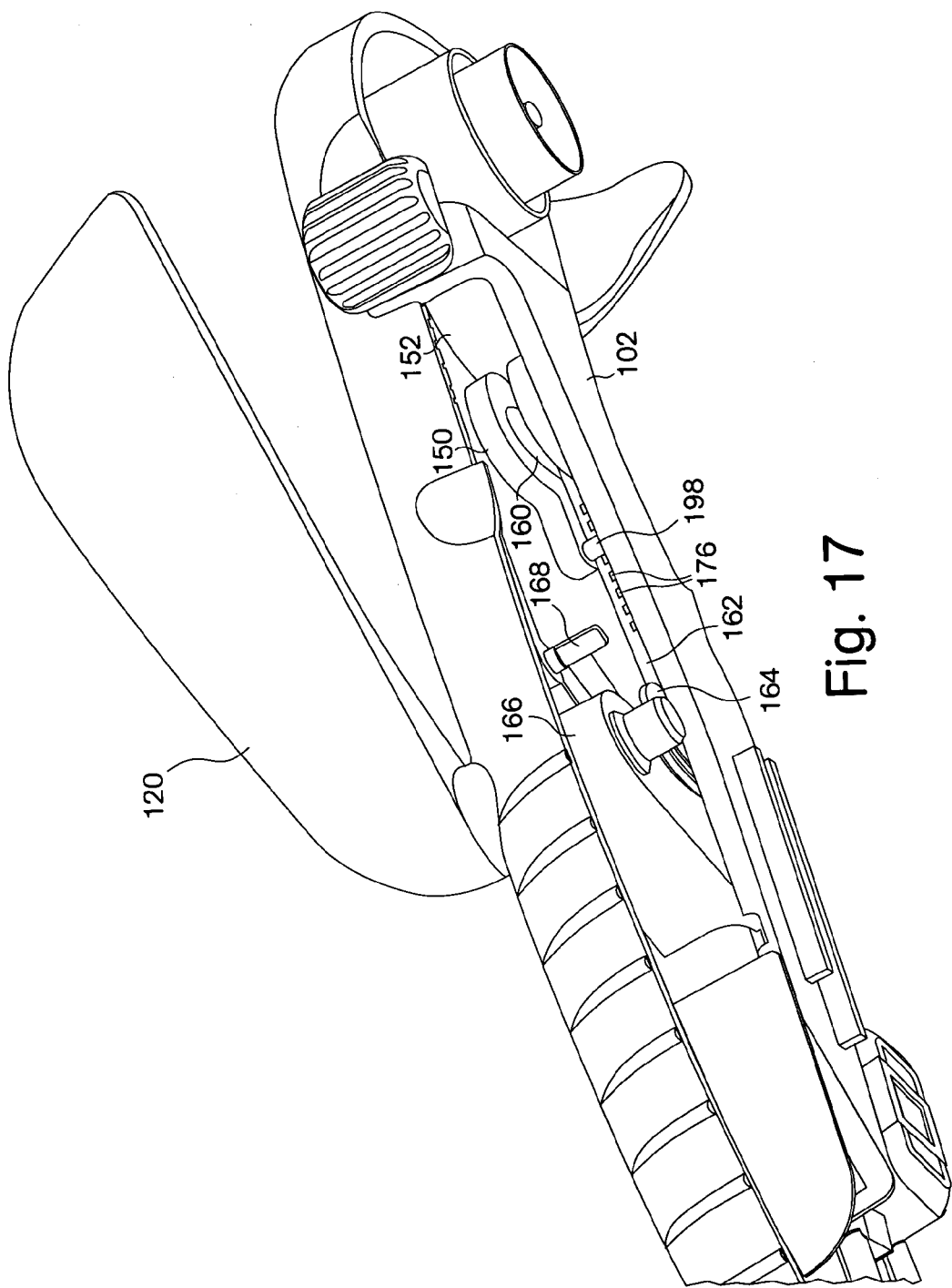
FIG. 17 is a top sectional view of the control handle detailing the arrangement of the flexible arch, strap and thumb lever components.
Figure 19:
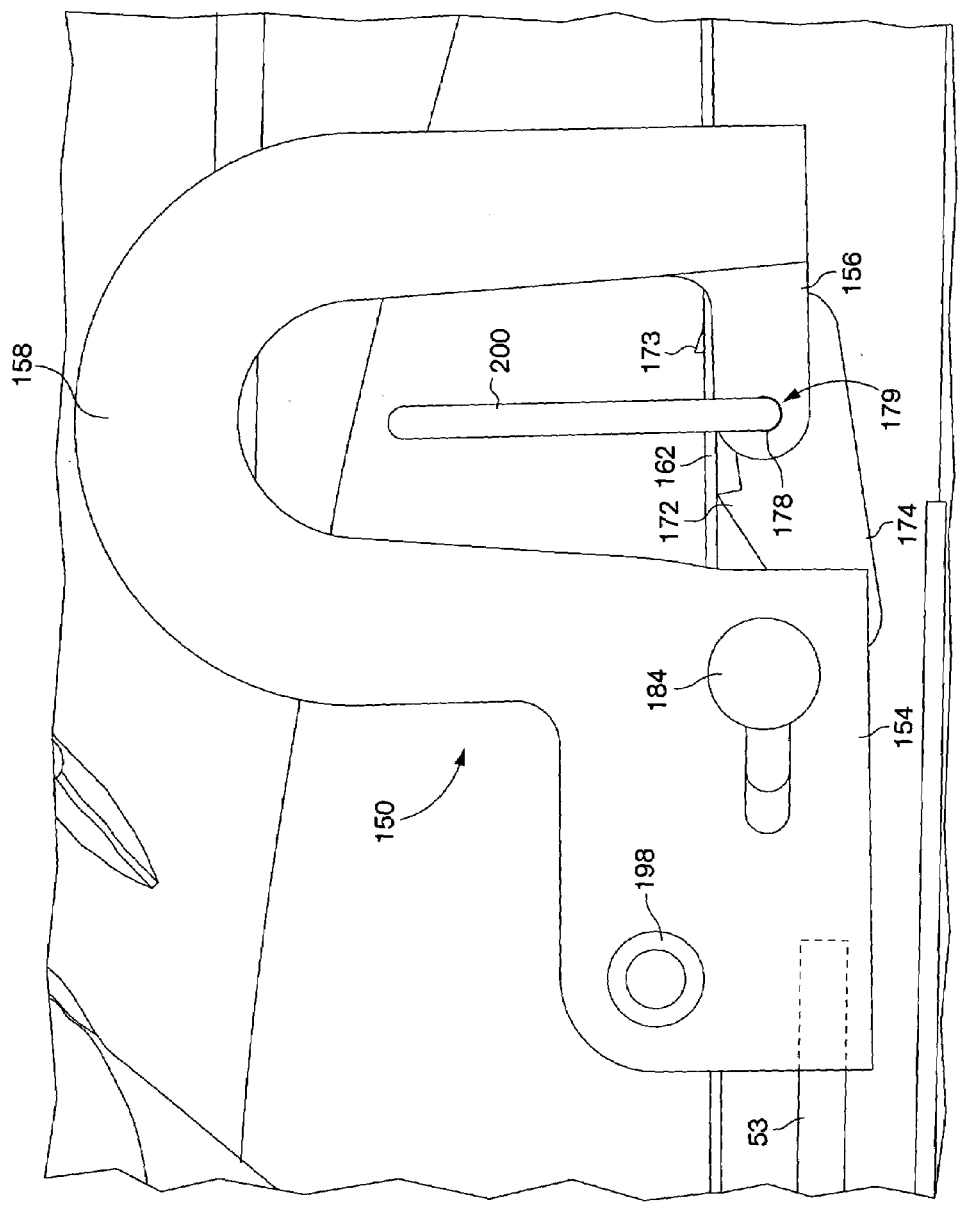
FIG. 19 is a detailed side view of the arch and associated components with the return tooth of the pawl engaged.
Figure 20:
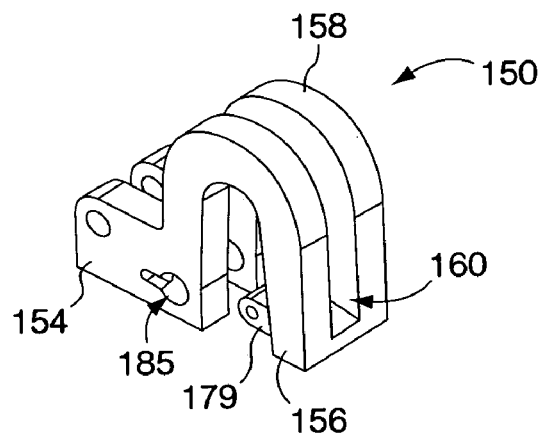
FIG. 20 is a detailed isometric view of the flexible arch.
Figure 21:
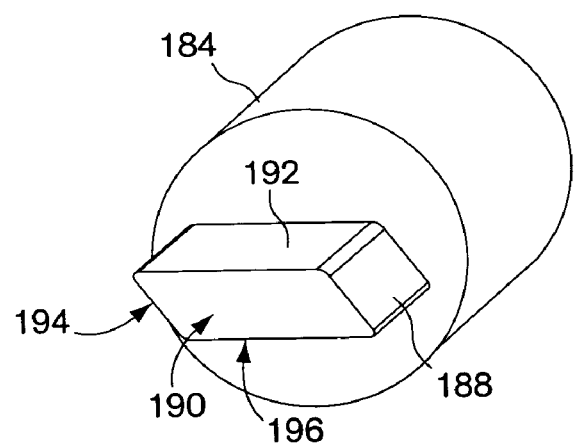
FIG. 21 is a detailed isometric view of a cam pin.
Figure 22:
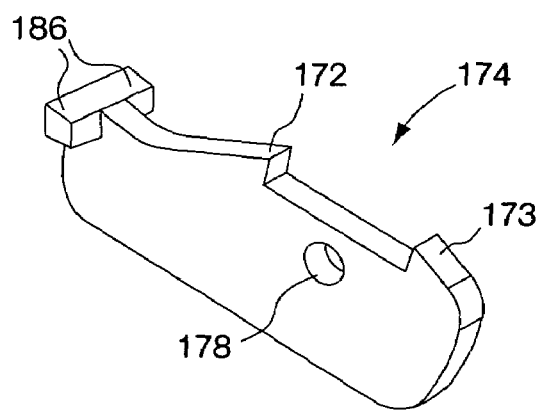
FIG. 22 is a detailed isometric view of the pawl.

FIG. 15 shows an alternate arrangement in the control handle 14 for providing automatic return of the band driver that differs from the releasable hitch arrangement described above in connection with FIGS. 14A and 14B. In this arrangement, the automatic return arrangement is provided by a flexible arch 150, which modulates the return force supplied to the band driver by flat coil spring 152. The arch is shown in detail in FIGS. 18, 19 and 20 and comprises a generally U shaped structure having a cam foot 154, a ball foot 156 and a flexible bridge 158 that extends between them. A slot 160 is formed lengthwise through the center of the flexible arch to permit sliding passage of a flexible strap that joins the return spring 152 to the thumb lever 120. As shown in FIGS. 15 through 17, a flexible strap 162 is joined to the free end of the flat rolled coil spring 152, extends through the slot 160 of the flexible arch, wraps around pulley 164 rotatably mounted to the outer edge of cam 166 and is anchored at anchor point 168.

As with the previous embodiment, thumb lever 120 is connected through the handle body 80 to cam 166. Therefore, when the thumb lever 120 is depressed, cam 166 rotates. As the cam rotates, the pulley 164 mounted along its near outer edge moves through an arch shaped path (leftward as shown in FIG. 15) that serves to pull strap 162 (also leftward as shown in FIG. 15). As the strap 162 is pulled, the flat rolled coil 152 uncoils slightly from its spool 170 rotatably mounted to sidewall of handle body 80. The uncoiling spring provides return tension to the strap 162.

The longitudinal movement of the strap 162 generated by depression of the thumb lever as described above, is translated to longitudinal movement of the band driver wire 53, which is fixed to the cam foot 154 of flexible arch and ultimately to the band driver. The flexible arch 150 is moved by the strap by the intermittent engagement of a pawl 174 mounted to the pawl foot 156 of the arch. Teeth of the pawl engage square drive holes 176 that are formed along the length of strap 162 as best seen in FIGS. 16 and 17. The pawl is mounted to the hinge mount 179 of hinge foot 156 at hinge point 178 allowing it to pivot so that one of its two teeth 172 and 173 becomes engaged with the square drive holes 176 of the strap depending on whether the strap is moving in the driving direction (leftward in FIG. 15) or in the return direction (rightward in FIG. 15).

Figure 18:
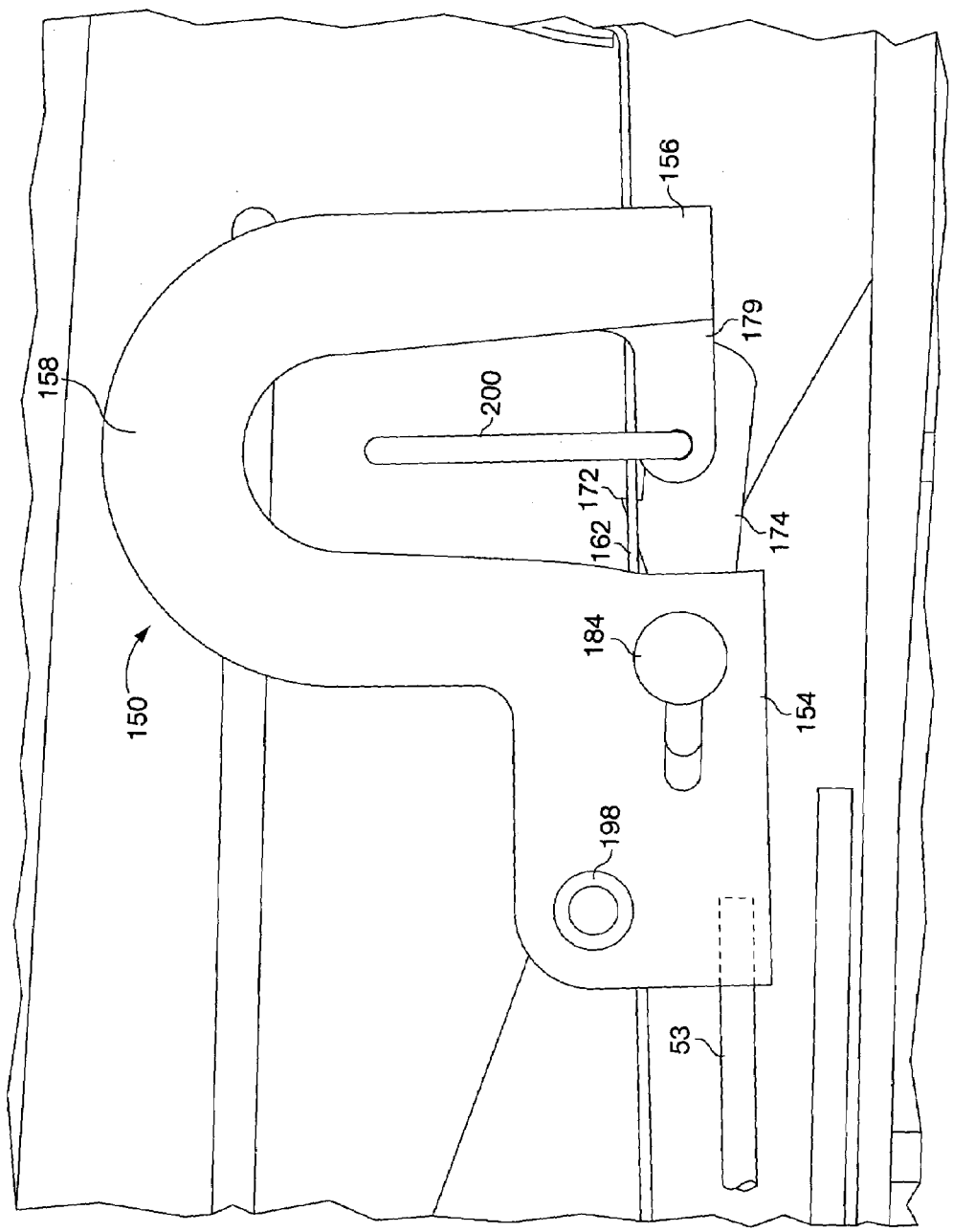
FIG. 18 is a detailed view of the flexible arch and related components with the drive tooth of the pawl engaged.

FIG. 18 shows a detailed drawing of the flexible arch 150 and pawl 174 with its drive tooth 172 engaged in a drive hole 176 of strap 162, which is being driven leftward by the depression of the thumb paddle (not shown). The pawl 174 is biased to tilt the drive tooth 172 into engagement with the strap by virtue of engagement of the pawl's cam wings 186 with the first surface 188 of the around-the-world cam 190 presented on the interior side of cam pins 184. Two cam pins 184 are mounted in cam pin holes 185 formed in cam foot 154 of the arch on each side of the slot 160 such that the around-the-world cam surface 190 faces inward to the slot. The around-the-world cam is essentially parallellagram shaped, and has four sides corresponding to four 4 situations experienced by the pawl. Pawl 174 rotatably mounted at hinge point 178 to the hinge mount 179 of the pawl foot portion 156 of the arch is positioned so that cam wings 186 just engage the first surface 188 of cam 190 when the arch is in its relaxed position. Because the initial engagement of cam wings 186 on first surface 188 of the cam biases the pawl 174 to have drive tooth 172 pushed upward in engagement with the strap 162, the initial motion of the strap leftward upon depression of the paddle 120 causes immediate leftward movement of the entire arch assembly 150 (leftward in the figures) to drive the driver wire 53 distally to move the band driver to eject a band. It is noted that the drive tooth is shaped to present a perpendicular profile to the square drive hole when the band is driving (moving leftward) and is sloped to ensure disengagement of the tooth when the strap is moving in the return direction (rightward in the figures). The release tooth is configured in the opposite manner.

Once the band driver reaches the end of travel on the band carrier as explained above, the driver wire stops moving and because of the engagement of the pawl, continued downward pressure on the thumb paddle 120 increases tension on the strap 162. As the strap continues to pull on drive tooth 172 the flexible bridge 158 begins to flex and permit travel of the pawl foot 156 towards cam foot 154. The flexure of bridge 158 and movement of pawl foot 156 toward the cam foot 154 of the arch causes the cam wings 186 on the pawl to ride up and along the second surface 192 of the around the world cam 190, which biases the drive tooth 172 upward into engagement with the strap 162 due to the hinged mounting of the pawl 174. Continued driving movement applied to the thumb paddle 120 causes continued movement of the pawl foot 156 toward the cam foot of the arch 150 until the cam wings 186 reach the end of the second cam surface 192 then drop downward along third cam surface 194 which serves to rotate the entire pawl 174 about its hinge point 178 so that drive tooth 172 drops downward out of engagement from the square drive holes 176 of strap 162. The rotation of the cam 174 at this moment also serves to raise the return tooth 173 upward into engagement with the drive holes of the strap to place the arch mechanism in readiness for the return stroke that will bring the band driver back into position behind the next ligation band to be delivered.

The transition from the second cam surface 192 to the third cam surface 194 and release of the drive tooth 172 from the strap 162 serves several other important functions. First, the engagement of the surfaces and release of the drive tooth 172 produce an audible click and a tactile feel to the user indicating that the band driver has reached its maximum extension and a band has been delivered to the intended tissue location. It also signals to the user to release the thumb paddle. Additionally, the flexure of the arch is calibrated to a force that maintains safe stresses on all components of the system so that the second cam surface 192 will be traversed and drive tooth 172 released from engagement before any of the components are fractured. If the release mechanism embodied in the arch system were not present, continued pressure on the thumb paddle 120 by the user may fracture components in the system, possibly causing the band driver to remain extended, which would interfere with completion of the procedure.

After the release of the drive tooth 172 as described above, the user will begin to release the thumb paddle 120 to prepare for firing of another band. As the thumb paddle is released upward, the cam 166 rotates in a rightward direction as shown in FIG. 15, causing the pulley 164 to also move rightward, which releases tension on the strap 162. As the tension on the strap 162 is released, return spring 152 applies return tension to pull the strap rightward. Now, with the return tooth 173 engaged with the strap, the arch mechanism 150 is pulled rightward, which serves to draw the driver wire 53 and band driver proximally. As the band driver engages the next ligation band on the band carrier as described above, the proximal motion of the band driver stops as does the rightward motion of driver wire 53 as shown in FIGS. 15 through 19. Continued return force applied by the coil spring 152 pulls on the strap 162 and engaged return tooth 173 which serves to flex the bridge 158 of arch as the pawl foot 156 is pulled rightward relative to the cam foot 154 as shown in figure. The relative motion between the pawl foot 156 and cam foot 154 causes the cam wings 186 of the pawl to move along the fourth cam surface 196, which maintains the pawl pivoted such that the return tooth is in engagement with the strap. Eventually, the cam wings 186 reach the end of the fourth cam surface 196 and pop up against the first cam surface 188. Engagement with the first cam surface serves to pivot the pawl 176 so that the return tooth 173 disengages from the strap and the drive tooth 172 again becomes engages in readiness for the driving direction of the next band.

The arch configuration also serves to limit the return forces applied to the band driver to safe limits. The flexure of the bridge 158 of the arch is predetermined to be sufficient to return the band driver but calculated to flex before damaging forces are applied to the band driver. If left unchecked the force of the return spring might pull the band driver proximally with such force that the additional bands waiting in readiness on the band carrier may be pulled out of position unintentionally. For the ligation device described herein, the arch strength has been engineered to yield at about seven pounds of force applied to the pawl foot. However that figure is provided only as an example of the level of force accepted before yielding that can be accommodated by the arch and is not meant to limit the scope of the invention in any way. Disengagement of the return tooth also provides an audible and tactile signal to the user that the band driver has returned to readiness to release another band.

Figure 23:
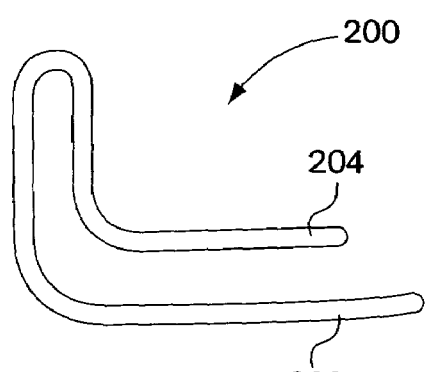
FIG. 23 is a detailed side view of the hinge pin.

It is noted that the strap 162 is maintained in engagement with the drive tooth 172 and return tooth 173 by support pin 198, which passes through cam foot of the arch 150 slightly above the strap pathway. The pin restrains the strap from upward movement away from the pawl teeth. Additionally, a hinge pin 200, shown in FIG. 23 is configured not only to provide a hinge 202 that passes through the hinge mount 179 and hinge point 178 of the pawl, but also includes a guide bar 204 that resides just above the strap pathway to restrain upward movement of the strap when the hinge pin 200 is in place.

It should be understood however, that the foregoing description of the invention is intended merely to be illustrative thereof and that other modifications, embodiments and equivalents may be apparent to those who are skilled in the art without departing from its spirit.

Having thus described the invention what we desire to claim and secure by Letters Patent is:

1. An endoscopic band ligator comprising:
   an inner sleeve mountable over an endoscope shaft;
   a middle sleeve longitudinally slidable relative to the inner sleeve and carrying at least one ligating band about its outer surface;
   an outer sleeve slidable relative to the middle and inner sleeves and having projecting fingers to engage in discharging a ligating band from the middle sleeve.

2. An endoscopic band ligator as defined in claim 1 wherein the middle sleeve further comprises at least one angled circumferential ridge formed on an exterior surface of the sleeve in relation to which the at least one band can be seated.

3. An endoscopic band ligator as defined in claim 2 wherein the middle sleeve further comprises longitudinal channels traversing the at least one circumferential ridge in which the projecting fingers of the outer sleeve may slide.

4. The endoscopic band ligator of claim 3, comprising two longitudinal channels, 180° apart.

5. The endoscopic band ligator of claim 3, wherein each finger is comprised of a resilient arm configured to slide within a longitudinal channel.

6. The endoscopic band ligator of claim 5, wherein each finger is further comprised of a radially inwardly directed protrusion on the resilient arm having a distal face configured to engage a band mounted on the middle sleeve.

7. The endoscopic band ligator of claim 1, wherein the middle and outer sleeves are made from one or more transparent materials.

8. The endoscopic band ligator of claim 1, wherein the inner sleeve has a small diameter portion that steps up to a large diameter portion at the proximal end of the sleeve.

9. The endoscopic band ligator of claim 8, wherein an annular vacuum seal is fitted into the large diameter portion of the inner sleeve.

10. The endoscopic band ligator of claim 1, wherein the distal tip of the inner sleeve has a radially inward projecting lip sufficiently deep to catch the distal face of an endoscope inserted therein.

11. The endoscopic band ligator of claim 1 wherein the middle sleeve has a plurality of circumferential saw-tooth ridges extending along its length, wherein the distal side of each ridge is of a greater diameter than the proximal side, and wherein there is a land between the proximal and distal ends of each ridge configured to receive a ligating band.

12. The endoscopic band ligator of claim 1, wherein the inside surface of the outer sleeve comprises longitudinally extending and radially spaced ribs.

13. A method of endoscopically applying a ligating band comprising:

(a) providing an endoscopic band ligator assembly comprising three coaxially arranged sleeves, wherein the inner sleeve is configured to be mounted over the distal end of an endoscope shaft, the middle sleeve is longitudinally slidable relative to the inner sleeve and carries at least one ligating band about its outer surface, and the outer sleeve is slidable relative to the middle and inner sleeves and has projecting fingers configured to discharge a ligating band from the middle sleeve;

(b) mounting the inner sleeve over the distal end of an endoscope shaft;

(c) navigating the endoscope to a treatment site with the middle and outer sleeves retracted proximally from the distal face of the endoscope;

(d) extending the middle and outer sleeves distally relative to the inner sleeve and the distal face of the endoscope at the treatment site to create a vacuum chamber;

(f) aspirating a tissue portion into the vacuum chamber;

(g) sliding the outer sleeve distally relative to the middle cylinder to push a ligating band from the middle sleeve onto the tissue.

14. The method of claim 13, further comprising:

(h) moving the outer sleeve proximally back along the middle sleeve such that the fingers ride over a next distal ligating band and become positioned just proximal to the band in readiness to push the band distally off the middle sleeve with the next distal movement of the outer sleeve.

* * * * *